(12) United States Patent
Grammenos et al.

(10) Patent No.: US 7,786,043 B2
(45) Date of Patent: Aug. 31, 2010

(54) 2-(PYRIDIN-2-YL)-PYRIMIDINES AND THEIR USE FOR CONTROLLING HARMFUL FUNGI

(75) Inventors: Wassilios Grammenos, Ludwigshafen (DE); Thomas Grote, Wachenheim (DE); Carsten Blettner, Hong Kong (CN); Markus Gewehr, Kastellaun (DE); Udo Hünger, Mainz (DE); Bernd Müller, Frankenthal (DE); Joachim Rheinheimer, Ludwigshafen (DE); Peter Schäfer, Ottersheim (DE); Frank Schieweck, Heßheim (DE); Anja Schwögler, Mannheim (DE); Ulrich Schöfl, Brühl (DE); Harald Köhle, Bobenheim (DE); Siegfried Strathmann, Limburgerhof (DE); Maria Scherer, Godramstein (DE); Reinhard Stierl, Freinsheim (DE); Jan Rether, Kaiserslautern (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/632,342

(22) PCT Filed: Jul. 22, 2005

(86) PCT No.: PCT/EP2005/008039

§ 371 (c)(1),
(2), (4) Date: Jan. 12, 2007

(87) PCT Pub. No.: WO2006/010570

PCT Pub. Date: Feb. 2, 2006

(65) Prior Publication Data

US 2008/0027085 A1    Jan. 31, 2008

(30) Foreign Application Priority Data

Jul. 23, 2004  (DE)  ....................... 10 2004 035 736

(51) Int. Cl.
| C07D 239/74 | (2006.01) |
| C07D 239/70 | (2006.01) |
| C07D 401/04 | (2006.01) |
| C07D 403/04 | (2006.01) |
| A01N 43/54 | (2006.01) |
| C07D 213/16 | (2006.01) |
| C07D 213/84 | (2006.01) |
| C07D 213/53 | (2006.01) |
| C07D 213/61 | (2006.01) |
| C07D 213/26 | (2006.01) |

(52) U.S. Cl. ............. 504/240; 544/253; 544/284; 546/348; 546/286; 546/332; 546/288; 546/345; 546/346

(58) Field of Classification Search ......... 544/253; 514/258.1; 504/240

See application file for complete search history.

(56) References Cited

U.S. PATENT DOCUMENTS

| 4,752,608 A | 6/1988 | Katoh et al. |
| 4,783,466 A | 11/1988 | Katoh et al. |
| 4,873,248 A | 10/1989 | Katoh et al. |
| 5,185,339 A * | 2/1993 | Pilkington et al. .......... 514/256 |

FOREIGN PATENT DOCUMENTS

| EP | 0 234 104 A2 | 9/1987 |
| EP | 0 259 139 A2 | 3/1988 |
| EP | 0 259 139 A2 | 3/1988 |
| JP | 64-83 A | 1/1989 |
| JP | 2-131479 A | 5/1990 |
| JP | 4-224580 A | 8/1992 |
| JP | 4-368301 A | 12/1992 |

OTHER PUBLICATIONS

Baldwin et al., Pesticide Science, Elsevier Applied Science Publisher. Barking, GB, vol. 44, No. 1, May 1, 1995, pp. 81-83.

* cited by examiner

*Primary Examiner*—James O Wilson
*Assistant Examiner*—Cecilia M Jaisle
(74) *Attorney, Agent, or Firm*—Birch, Stewart, Kolasch & Birch, LLP

(57) ABSTRACT

The invention relates to 2-(pyridin-2-yl)-pyrimidine compounds of general formula (I) and their use for controlling pathogenic fungi and as plant protection products that, as an active constituent, contain compounds of this type:

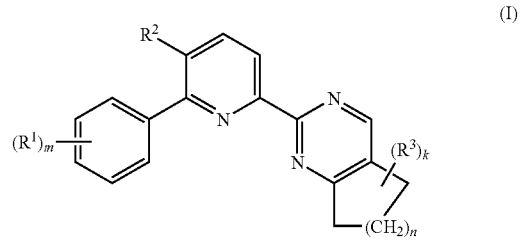

In general formula (I), k represents 0, 1, 2, 3; m represents 0, 1, 2, 3, 4 or 5; n represents 1, 2, 3, 4 or 5; $R^1$, independent of one another, represents halogen, OH, CN, $NO_2$, $C_1$-$C_4$ alkyl, $C_1$-$C_4$ alkyl halide, $C_1$-$C_4$ alkoxy, $C_1$-$C_4$ alkoxy halide, $C_2$-$C_4$ alkenyl, $C_2$-$C_4$ alkynyl, $C_3$-$C_8$ cycloalkyl, $C_1$-$C_4$ alkoxy-$C_1$-$C_4$ alkyl, amino, phenoxy, which is optionally substituted by halogen or $C_1$-$C_4$ alkyl, NHR, $NR_2$, $C(R^a)=N-OR^b$, $S(=O)_pA^1$ or $C(=O)A^2$, or two radicals $R^1$ bound to adjacent carbon atoms can, together, also represent a group —O-Alk-O—, wherein Alk represents a linear or branched $C_1$-$C_4$ alkylene, and 1, 2, 3 or 4 hydrogen atoms can also be replaced by halogen; $R^2$ represents $C_1$-$C_4$ alkyl halide, $C_1$-$C_4$ alkoxy, $C_1$-$C_4$ alkoxy halide, hydroxy, halogen, CN or $NO_2$; whereby $R^2$ can also represent hydrogen or $C_1$-$C_4$ alkyl when at least one of the three following conditions is fulfilled: n represents 3, 4 or 5; k represents 1, 2 or 3; if m is not equal to 0, at least one of the radicals $R^1$ represents a radical that differs from halogen, $C_1$-$C_4$ alkyl, $C_1$-$C_4$ alkoxy and $C_1$-$C_4$ alkyl halide, and; $R^3$ represents $C_1$-$C_4$ alkyl.

13 Claims, No Drawings

2-(PYRIDIN-2-YL)-PYRIMIDINES AND THEIR USE FOR CONTROLLING HARMFUL FUNGI

The present invention relates to 2-(pyridin-2-yl)pyrimidines and to their use for controlling harmful fungi, and also to crop protection compositions comprising such compounds as an effective component.

EP-A 234 104 describes 2-(pyridin-2-yl)pyrimidines which have an alkyl group in the 6-position of the pyridine radical and which may have a fused saturated 5- or 6-membered ring in the 3,4-position of the pyrimidine ring. The compounds are suitable for controlling phytopathogenic fungi (harmful fungi).

U.S. Pat. No. 4,873,248 discloses 2-(pyridin-2-yl)pyrimidines having fungicidal action which carry an optionally substituted phenyl ring in the 4-position of the pyrimidine ring.

EP-A 259 139 describes 2-(pyridin-2-yl)pyrimidines of the formula A

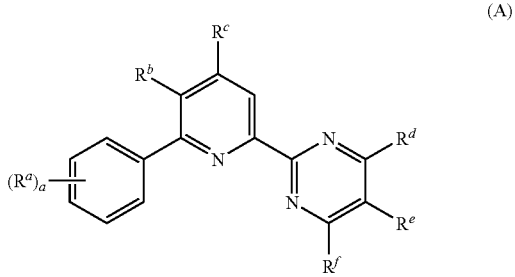

(A)

in which a is 0, 1, 2, 3, 4 or 5, $R^a$ is halogen, lower alkyl, lower alkoxy or haloalkyl, $R^b$ and $R^c$ independently of one another are hydrogen or $C_1$-$C_4$-alkyl, $R^d$ is hydrogen or lower alkyl, $R^e$ is hydrogen, lower alkyl or halogen or together with $R^d$ is propane-1,3-diyl or butane-1,4-diyl and $R^f$ is inter alia hydrogen, alkyl, lower alkoxy or lower alkylthio.

With respect to their fungicidal action, some of the 2-(pyridin-2-yl)pyrimidines known from the prior art are unsatisfactory, or they have unwanted properties, such as poor compatibility with useful plants.

Accordingly, it is an object of the present invention to provide novel compounds having improved fungicidal activity and/or better compatibility with useful plants.

Surprisingly, this object is achieved by 2-(pyridin-2-yl) pyrimidine compounds of the formula I

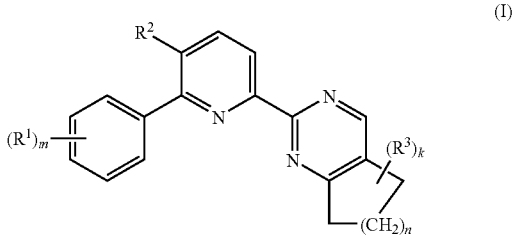

(I)

in which:
k is 0, 1, 2 or 3;
m is 0, 1, 2, 3, 4 or 5;
n is 1, 2, 3, 4 or 5;

$R^1$ independently of one another are halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_3$-$C_8$-cycloalkyl, $C_1$-$C_4$-alkoxy-$C_1$-$C_4$-alkyl, amino, phenoxy which is optionally substituted by halogen or $C_1$-$C_4$-alkyl, NHR, $NR_2$, $C(R^a)$=N—$OR^b$, $S(=O)_pA^1$ or $C(=O)A^2$, where p, R, $R^a$, $R^b$, $A^1$ and $A^2$ are as defined below:
R is $C_1$-$C_4$-alkyl or $C_1$-$C_4$-alkylcarbonyl,
$R^a$ is hydrogen or $C_1$-$C_4$-alkyl,
$R^b$ is $C_1$-$C_4$-alkyl, $C_3$-$C_4$-alkenyl or $C_3$-$C_4$-alkynyl,
p is 0, 1 or 2,
$A^1$ is $C_1$-$C_4$-alkyl or for p=2 also $NH_2$, $C_1$-$C_4$-alkylamino or di-($C_1$-$C_4$-alkyl)amino, and
$A^2$ is hydrogen, hydroxyl, $C_1$-$C_4$-alkyl, $C_1$-$C_4$-alkylamino, di-($C_1$-$C_4$-alkyl)amino, $C_2$-$C_4$-alkenyl, $C_1$-$C_4$-alkoxy or $C_1$-$C_4$-haloalkoxy;
or two radicals $R^1$ attached to adjacent carbon atoms together may also be a group —O-Alk-O— where Alk is straight-chain or branched $C_1$-$C_4$-alkylene and where 1, 2, 3 or 4 hydrogen atoms may also be replaced by halogen;
$R^2$ is $C_1$-$C_4$-haloalkyl, $C_1$-$C_4$-alkoxy, $C_1$-$C_4$-haloalkoxy, hydroxyl, halogen, CN or $NO_2$; where $R^2$ may also be hydrogen or $C_1$-$C_4$-alkyl if at least one of the following three conditions is met:
n is 3, 4 or 5,
k is 1, 2 or 3,
for m≠0 at least one of the radicals $R^1$ is a radical different from halogen, $C_1$-$C_4$-alkyl, $C_1$-$C_4$-alkoxy and $C_1$-$C_4$-haloalkyl; and
$R^3$ is $C_1$-$C_4$-alkyl;

and by the agriculturally acceptable salts of the compounds I.

The present invention therefore provides 2-(pyridin-2-yl) pyrimidines of the formula I and their agriculturally acceptable salts.

The present invention furthermore provides the use of the 2-(pyridin-2-yl)pyrimidines of the formula I and their agriculturally acceptable salts for controlling phytopathogenic fungi (=harmful fungi), and also a method for controlling phytopathogenic fungi which comprises treating the fungi or the materials, plants, the soil or seed to be protected against fungal attack with an effective amount of a compound of the formula I and/or with an agriculturally acceptable salt of I.

The present invention furthermore provides a composition for controlling harmful fungi, which compositions comprise at least one 2-(pyridin-2-yl)pyrimidine compound of the formula I and/or an agriculturally acceptable salt thereof and at least one liquid or solid carrier.

Depending on the substitution pattern, the compounds of the formula I and their tautomers may have one or more centers of chirality, in which case they are present as pure enantiomers or pure diastereomers or as enantiomer or diastereomer mixtures. The invention provides both the pure enantiomers or diastereomers and also their mixtures.

Suitable agriculturally useful salts are especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, and of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and also the anions of $C_1$-$C_4$-alkanoic acids, preferably formate, acetate, propionate and butyrate. They can be formed by reacting I with an acid of the corresponding anion, preferably of hydrochloric acid, hydrobromic acid, sulfuric acid, phosphoric acid or nitric acid.

In the definitions of the variables given in the formulae above, collective terms are used which are generally representative of the substituents in question. The term $C_n$-$C_m$ denotes the number of carbon atoms in the substituent or substituent moiety possible in each case:

halogen: fluorine, chlorine, bromine and iodine;

alkyl and all alkyl moieties in alkoxy, alkoxyalkyl, alkylamino and dialkylamino: saturated straight-chain or branched hydrocarbon radicals having 1 to 4 carbon atoms, for example $C_1$-$C_4$-alkyl, such as methyl, ethyl, propyl, 1-methylethyl, butyl, 1-methylpropyl, 2-methylpropyl, 1,1-dimethylethyl;

haloalkyl: straight-chain or branched alkyl groups having 1 to 4 carbon atoms (as mentioned above), where some or all of the hydrogen atoms in these groups may be replaced by halogen atoms as mentioned above and in particular by fluorine or chlorine, in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

alkenyl: monounsaturated straight-chain or branched hydrocarbon radicals having 2 to 4 or 3 to 4 carbon atoms and one double bond in any position, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl;

alkynyl: straight-chain or branched hydrocarbon groups having 2 to 4 or 3 to 4 carbon atoms and a triple bond in any position, for example ethynyl, 1-propynyl, 2-propynyl, 1-butynyl, 2-butynyl, 3-butynyl, 1-methyl-2-propynyl;

cycloalkyl: monocyclic saturated hydrocarbon groups having 3 to 8, preferably up to 6, carbon ring members, such as cyclopropyl, cyclobutyl, cyclopentyl and cyclohexyl;

alkylamino: an alkyl group attached via an NH group, in which alkyl is one of the above-mentioned alkyl radicals having 1 to 4 carbon atoms, such as methylamino, ethylamino, n-propylamino, isopropylamino, n-butylamino and the like;

dialkylamino: a radical of the formula N(alkyl)$_2$ in which alkyl is one of the above-mentioned alkyl radicals having 1 to 4 carbon atoms, for example dimethylamino, diethylamino, methylethylamino, N-methyl-N-propylamino and the like;

$C_1$-$C_4$-alkoxy: an alkyl group which is attached via oxygen and has 1 to 4 carbon atoms, for example methoxy, ethoxy, n-propoxy, 1-methylethoxy, butoxy, 1-methylpropoxy, 2-methylpropoxy or 1,1-dimethylethoxy;

$C_1$-$C_4$-haloalkoxy: a $C_1$-$C_4$-alkoxy radical as mentioned above which is partially or fully substituted by fluorine, chlorine, bromine and/or iodine, preferably by fluorine, i.e., for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, alkylene: a straight-chain saturated hydrocarbon chain having 2 to 6 and in particular 2 to 4 carbon atoms, such as ethane-1,2-diyl, propane-1,3-diyl, butane-1,4-diyl, pentane-1,5-diyl or hexane-1,6-diyl.

A first embodiment of the invention relates to compounds in which n is 3, 4 or 5 and in particular 3 or 4, $R^2$ is hydrogen, $C_1$-$C_4$-alkyl, $C_1$-$C_4$-haloalkyl, $C_1$-$C_4$-alkoxy, $C_1$-$C_4$-haloalkoxy, hydroxyl, halogen, CN or $NO_2$ and the other variables have the meanings mentioned above, in particular the meanings mentioned below as being preferred.

A second embodiment of the invention relates to compounds in which n is 1 or 2 and in particular 2, $R^2$ is $C_1$-$C_4$-haloalkyl, $C_1$-$C_4$-alkoxy, $C_1$-$C_4$-haloalkoxy, hydroxyl, halogen, CN or $NO_2$ and the other variables have the meanings mentioned above, in particular the meanings mentioned below as being preferred.

With a view to the use as fungicides, preference is given to those compounds of the formula I in which the variables m, n, k, $R^1$, $R^2$ and $R^3$ independently of one another and in particular in combination have the meanings below.

m is 0 or an integer 1, 2 or 3;

n is 1, 2 or 3, especially 2 or 3;

k is 0, 1 or 2, especially 0. If k is different from 0, the radical(s) $R^3$ can be located in any position of the saturated fused ring. In a particularly preferred embodiment, k is 0. In a further preferred embodiment, k is 2. In this embodiment, the two radicals $R^3$ are preferably located at the same carbon atom.

$R^1$ is halogen, in particular fluorine, chlorine or bromine, cyano, OH, CHO, $NO_2$, $NH_2$, methylamino, dimethylamino, diethylamino, $C_1$-$C_4$-alkyl, in particular methyl, isopropyl or tert-butyl, $C_3$-$C_8$-cycloalkyl, especially cyclopropyl, cyclopentyl or cyclohexyl, $C_1$-$C_4$-alkoxy, especially $OCH_3$, $C_1$-$C_4$-alkylthio, especially methylthio or ethylthio, $C_1$-$C_4$-haloalkyl, in particular $C_1$-$C_2$-fluoroalkyl, especially $CF_3$, $C_1$-$C_4$-haloalkoxy, especially $OCHF_2$ or $OCF_3$, or $CO(A^2)$ where $A^2$ is $C_1$-$C_4$-alkoxy, especially $OCH_3$, or a $C_1$-$C_4$-alkyl, especially methyl. Preference is also given to compounds in which one of the radicals $R^1$ is a group $C(R^a)$=$NOR^b$ in which $R^a$ and $R^b$ are as defined above and in which $R^a$ is in particular H or $CH_3$ and $R^b$ is in particular $C_1$-$C_4$-alkyl, propargyl or allyl. Particularly preferably $R^1$ is selected from among halogen, in particular F or Cl, CN, $C_1$-$C_4$-alkyl, in particular methyl, isopropyl or tert-butyl, $C_1$-$C_4$-haloalkyl, in particular $C_1$-$C_2$-fluoroalkyl, especially trifluoromethyl, $C_1$-$C_4$-alkoxy, in particular methoxy, ethoxy, isopropyloxy, $C_1$-$C_4$-alkylthio, e.g. methylthio, or $C_1$-$C_4$-haloalkoxy, in particular $OCF_3$ or $OCHF_2$ or one of the radicals is a group $C(R^a)$=NO—$R^b$ or a group C(O)-$A^2$.

Very particularly preferred radicals $R^1$ are selected from the group consisting of methyl, F, Cl, methoxy, trifluoromethyl and CN. Likewise particularly preferred radicals are selected from the group consisting of CH(=NOCH$_3$), C(CH$_3$)(=N—OCH$_3$), C(CH$_3$)(=N—OC$_2$H$_5$), C(O)CH$_3$ and CO$_2$CH$_3$.

R$^2$ is C$_1$-C$_4$-haloalkyl, preferably C$_1$-C$_2$-fluoroalkyl and especially trifluoromethyl, C$_1$-C$_4$-alkoxy, C$_1$-C$_4$-haloalkoxy, halogen, CN or NO$_2$, in particular C$_1$-C$_4$-alkoxy, especially methoxy or ethoxy, C$_1$-C$_4$-haloalkyl, in particular trifluoromethoxy or difluoromethoxy, or halogen, especially F, Cl or Br.

Preference is also given to compounds of the formula I where n=3, 4 or 5 in which R$^2$ is hydrogen or in particular C$_1$-C$_4$-alkyl and particularly preferred methyl or ethyl.

Preference is likewise given to compounds of the formula I where k=1, 2 or 3 and especially 2, in which R$^2$ is hydrogen or in particular C$_1$-C$_4$-alkyl and particularly preferably methyl or ethyl.

R$^3$ is methyl or isopropyl.

Among the compounds of the formula I, particular preference is given to those in which the phenyl group substituted by (R$^1$)$_m$ is the group of the formula P

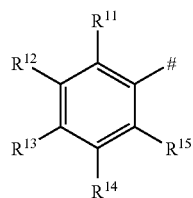

(P)

in which # is the point of attachment to the pyridine ring and R$^{11}$, R$^{12}$, R$^{13}$, R$^{14}$ and R$^{15}$ have the meanings given for R$^1$, in particular the meanings given as being preferred or particularly preferred. In a preferred embodiment, at least one and especially 1, 2, or 3 of the radicals R$^{11}$, R$^{12}$, R$^{13}$, R$^{14}$ and R$^{15}$ is different from hydrogen. In another preferred embodiment, all of the radicals R$^{11}$, R$^{12}$, R$^{13}$, R$^{14}$ and R$^{15}$ are hydrogen. In particular:

R$^{11}$ is hydrogen, fluorine, chlorine, CH$_3$, OCH$_3$, OCHF$_2$, OCF$_3$ or CF$_3$;

R$^{12}$, R$^{14}$ independently of one another are hydrogen, chlorine, fluorine, CH$_3$, OCH$_3$, OCHF$_2$, OCF$_3$ or CF$_3$, where one of the radicals R$^{12}$ and R$^{14}$ may also be NO$_2$, C(O)CH$_3$ or COOCH$_3$; in particular R$^{12}$ and R$^{14}$ are hydrogen, fluorine, methyl or trifluoromethyl;

R$^{13}$ is hydrogen, fluorine, chlorine, cyano, OH, CHO, NO$_2$, NH$_2$, methylamino, dimethylamino, diethylamino, C$_1$-C$_4$-alkyl, especially CH$_3$, C$_2$H$_5$, CH(CH$_3$)$_2$, C$_3$-C$_8$-cycloalkyl, especially cyclopropyl, cyclopentyl or cyclohexyl, C$_1$-C$_4$-alkoxy, especially OCH$_3$, C$_1$-C$_4$-alkylthio, especially methylthio or ethylthio, C$_1$-C$_4$-haloalkyl, especially CF$_3$, C$_1$-C$_4$-haloalkoxy, especially OCHF$_2$ or OCF$_3$, or CO(A$^2$) in which A$^2$ is C$_1$-C$_4$-alkyl, especially methyl or C$_1$-C$_4$-alkoxy, especially OCH$_3$, or R$^{12}$ and R$^{13}$ together form a group O—CH$_2$—O; and R$^{15}$ is hydrogen, fluorine, chlorine or C$_1$-C$_4$-alkyl, especially CH$_3$, in particular hydrogen or fluorine.

Preference is also given to compounds in which R$^{12}$ or R$^{13}$ is a group C(R$^a$)=NOR$^b$ in which R$^a$ and R$^b$ have the meanings given above, in particular the meanings mentioned as being preferred.

If more than one of the radicals R$^{11}$, R$^{12}$, R$^{13}$, R$^{14}$ or R$^{15}$ is different from hydrogen, advantageously only one of the radicals different from hydrogen is different from halogen or methyl. Especially if one of the radicals R$^{11}$, R$^{12}$, R$^{13}$, R$^{14}$ or R$^{15}$ is different from hydrogen, halogen or methyl, the remaining radicals R$^{11}$, R$^{12}$, R$^{13}$, R$^{14}$, R$^{15}$ are selected from the group consisting of halogen and hydrogen.

Examples of radicals P are in particular those in which R$^{11}$, R$^{12}$, R$^{13}$, R$^{14}$ and R$^{15}$ together have the meanings given in one row of table A:

TABLE A

| | R$^{11}$ | R$^{12}$ | R$^{13}$ | R$^{14}$ | R$^{15}$ |
|---|---|---|---|---|---|
| 1 | H | H | H | H | H |
| 2 | F | H | H | H | H |
| 3 | H | F | H | H | H |
| 4 | H | H | F | H | H |
| 5 | Cl | H | H | H | H |
| 6 | H | Cl | H | H | H |
| 7 | H | H | Cl | H | H |
| 8 | Br | H | H | H | H |
| 9 | H | Br | H | H | H |
| 10 | H | H | Br | H | H |
| 11 | F | F | H | H | H |
| 12 | F | H | F | H | H |
| 13 | F | H | H | H | F |
| 14 | H | F | F | H | H |
| 15 | H | F | H | F | H |
| 16 | Cl | Cl | H | H | H |
| 17 | Cl | H | Cl | H | H |
| 18 | Cl | H | H | Cl | H |
| 19 | H | Cl | Cl | H | H |
| 20 | H | Cl | H | Cl | H |
| 21 | F | Cl | H | H | H |
| 22 | Cl | F | H | H | H |
| 23 | F | H | Cl | H | H |
| 24 | F | H | H | Cl | H |
| 25 | F | H | H | H | Cl |
| 26 | Cl | H | F | H | H |
| 27 | H | Cl | F | H | H |
| 28 | H | F | Cl | H | H |
| 29 | H | Cl | H | F | H |
| 30 | F | H | F | H | F |
| 31 | F | F | F | F | F |

TABLE A-continued

| | $R^{11}$ | $R^{12}$ | $R^{13}$ | $R^{14}$ | $R^{15}$ |
|---|---|---|---|---|---|
| 32 | $CF_3$ | H | H | H | H |
| 33 | H | $CF_3$ | H | H | H |
| 34 | H | H | $CF_3$ | H | H |
| 35 | F | Cl | H | Cl | H |
| 36 | F | H | Cl | Cl | H |
| 37 | F | H | H | Cl | Cl |
| 38 | Cl | H | H | H | $CF_3$ |
| 39 | Cl | H | H | $CF_3$ | H |
| 40 | Cl | H | $CF_3$ | H | H |
| 41 | $OCF_3$ | H | H | H | H |
| 42 | H | $OCF_3$ | H | H | H |
| 43 | H | H | $OCF_3$ | H | H |
| 44 | F | H | H | H | $OCF_3$ |
| 45 | F | H | H | $OCF_3$ | H |
| 46 | F | H | $OCF_3$ | H | H |
| 47 | Cl | H | H | H | $OCF_3$ |
| 48 | Cl | H | $OCF_3$ | H | H |
| 49 | $OHCF_2$ | H | H | H | H |
| 50 | H | $OCHF_2$ | H | H | H |
| 51 | H | H | $OCHF_2$ | H | H |
| 52 | F | H | H | H | $OCHF_2$ |
| 53 | F | H | $OCHF_2$ | H | H |
| 54 | Cl | H | H | $OCHF_2$ | H |
| 55 | Cl | H | $OCHF_2$ | H | H |
| 56 | $CH_3$ | H | H | H | H |
| 57 | H | $CH_3$ | H | H | H |
| 58 | H | H | $CH_3$ | H | H |
| 59 | F | H | H | H | $CH_3$ |
| 60 | F | H | H | $CH_3$ | H |
| 61 | F | H | $CH_3$ | H | H |
| 62 | H | F | $CH_3$ | H | H |
| 63 | H | $CH_3$ | F | H | H |
| 64 | F | $CH_3$ | H | H | H |
| 65 | $OCH_3$ | H | H | H | H |
| 66 | H | $OCH_3$ | H | H | H |
| 67 | F | H | H | H | $OCH_3$ |
| 68 | F | H | H | $OCH_3$ | H |
| 69 | F | H | $OCH_3$ | H | H |
| 70 | H | F | $OCH_3$ | H | H |
| 71 | Cl | H | H | H | $CH_3$ |
| 72 | Cl | H | $CH_3$ | H | H |
| 73 | H | H | $C_2H_5$ | H | H |
| 74 | H | H | $CH(CH_3)_2$ | H | H |
| 75 | H | H | $C(CH_3)_3$ | H | H |
| 76 | H | H | OH | H | H |
| 77 | H | H | $OCH_3$ | H | H |
| 78 | H | H | $OC_2H_5$ | H | H |
| 79 | H | H | $OCH(CH_3)_2$ | H | H |
| 80 | H | H | $OC(CH_3)_3$ | H | H |
| 81 | F | H | $OCH_3$ | H | H |
| 82 | F | H | $OC_2H_5$ | H | H |
| 83 | F | H | $OCH(CH_3)_2$ | H | H |
| 84 | F | H | $OC(CH_3)_3$ | H | H |
| 85 | H | F | $OCH_3$ | H | H |
| 86 | H | F | $OC_2H_5$ | H | H |
| 87 | H | F | $OCH(CH_3)_2$ | H | H |
| 88 | H | F | $OC(CH_3)_3$ | H | H |
| 89 | Cl | H | $OCH_3$ | H | H |
| 90 | Cl | H | $OC_2H_5$ | H | H |
| 91 | Cl | H | $OCH(CH_3)_2$ | H | H |
| 92 | Cl | H | $OC(CH_3)_3$ | H | H |
| 93 | H | Cl | $OCH_3$ | H | H |
| 94 | H | Cl | $OC_2H_5$ | H | H |
| 95 | H | Cl | $OCH(CH_3)_2$ | H | H |
| 96 | H | Cl | $OC(CH_3)_3$ | H | H |
| 97 | H | H | CHO | H | H |
| 98 | H | H | CN | H | H |
| 99 | H | H | $NO_2$ | H | H |
| 100 | H | $NO_2$ | H | H | H |
| 101 | H | H | $C(O)OCH_3$ | H | H |
| 102 | H | H | $C(O)OC_2H_5$ | H | H |
| 103 | H | H | $C(O)OCH(CH_3)_2$ | H | H |
| 104 | H | H | $C(O)OC(CH_3)_3$ | H | H |
| 105 | H | H | $NH_2$ | H | H |
| 106 | H | H | $NHCH_3$ | H | H |
| 107 | H | H | $N(CH_3)_2$ | H | H |
| 108 | H | H | $NHCH_2CH_3$ | H | H |

TABLE A-continued

| | $R^{11}$ | $R^{12}$ | $R^{13}$ | $R^{14}$ | $R^{15}$ |
|---|---|---|---|---|---|
| 109 | H | H | N(CH$_2$CH$_3$)$_2$ | H | H |
| 110 | H | H | SCH$_3$ | H | H |
| 111 | H | H | SO$_2$CH$_3$ | H | H |
| 112 | H | H | SCH$_2$CH$_3$ | H | H |
| 113 | H | H | SO$_2$CH$_2$CH$_3$ | H | H |
| 114 | H | H | c-C$_3$H$_5$ | H | H |
| 115 | H | H | c-C$_5$H$_9$ | H | H |
| 116 | H | H | c-C$_6$H$_{11}$ | H | H |
| 117 | H | | O—CH$_2$—O | | H |
| 118 | H | H | CH(=NOCH$_3$) | H | H |
| 119 | H | H | C(CH$_3$)(=NOCH$_3$) | H | H |
| 120 | H | SCH$_3$ | H | H | H |
| 121 | H | H | OCH$_2$CH$_2$CH$_3$ | H | H |
| 122 | H | H | C$_6$H$_5$O | H | H |
| 123 | H | H | C(O)CH$_3$ | H | H |
| 124 | H | H | C(CH$_3$)(=NOC$_2$H$_5$) | H | H |
| 125 | OC$_2$H$_5$ | H | H | H | H |
| 126 | CH$_3$ | CH$_3$ | H | H | H |
| 127 | CH$_3$ | H | F | H | H |
| 128 | OCH$_3$ | H | OCH$_3$ | H | H |
| 129 | F | H | H | F | H |
| 130 | CH$_3$ | H | H | CH$_3$ | H |
| 131 | H | OC$_2$H$_5$ | H | H | H |
| 132 | H | C(O)CH$_3$ | H | H | H |
| 133 | H | OCH(CH$_3$)$_2$ | H | H | H |
| 134 | H | C(CH$_3$)(=NOCH$_3$) | H | H | H |
| 135 | H | C(CH$_3$)(=NOC$_2$H$_5$) | H | H | H |
| 136 | H | CO$_2$CH$_3$ | H | H | H |
| 137 | H | CH$_3$ | CH$_3$ | H | H |
| 138 | H | OCH$_3$ | OCH$_3$ | H | H |
| 139 | H | CH$_3$ | Cl | H | H |
| 140 | H | CH$_3$ | OCH$_3$ | H | H |
| 141 | H | CH$_3$ | H | CH$_3$ | H |
| 142 | H | CF$_3$ | H | CF$_3$ | H |
| 143 | H | F | F | F | H |
| 144 | H | H | OCH$_2$CH$_2$CH$_3$ | H | H |

A particularly preferred embodiment of the invention is the compounds of the formula Ia

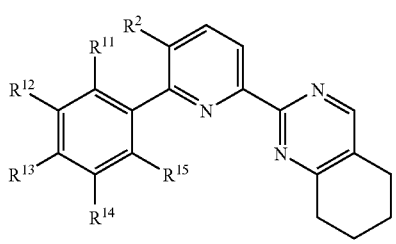

(Ia)

in $R^{11}$, $R^{12}$, $R^{13}$, $R^{14}$ and $R^{15}$ have the meanings mentioned above and in particular the meanings mentioned as being preferred and $R^2$ has the meanings mentioned above which are different from H and C$_1$-C$_4$-alkyl and is in particular C$_1$-C$_4$alkoxy, especially methoxy, ethoxy, isopropyloxy, tert-butyloxy, C$_1$-C$_2$-fluoroalkyloxy, especially difluoromethoxy or trifluoromethoxy, CN, NO$_2$ or OH. Examples of these compounds are the compounds of the formula Ia given in tables 1 to 9 below in which $R^{11}$, $R^{12}$, $R^{13}$, $R^{14}$ and $R^{15}$ together have the meanings given in one of rows 2 to 144 of table A.

Table 1:
Compounds of the formula Ia in which $R^2$ is methoxy and $R^{11}$, $R^{12}$, $R^{13}$, $R^{14}$ and $R^{15}$ together have the meanings given in one of rows 2 to 144 of table A.

Table 2:
Compounds of the formula Ia in which $R^2$ is ethoxy and $R^{11}$, $R^{12}$, $R^{13}$, $R^{14}$ and $R^{15}$ together have the meanings given in one of rows 2 to 144 of table A.

Table 3:
Compounds of the formula Ia in which $R^2$ is isopropyloxy and $R^{11}$, $R^{12}$, $R^{13}$, $R^{14}$ and $R^{15}$ together have the meanings given in one of rows 2 to 144 of table A.

Table 4:
Compounds of the formula Ia in which $R^2$ is tert-butyloxy and $R^{11}$, $R^{12}$, $R^{13}$, $R^{14}$ and $R^{15}$ together have the meanings given in one of rows 2 to 144 of table A.

Table 5:
Compounds of the formula Ia in which $R^2$ is trifluoromethoxy and $R^{11}$, $R^{12}$, $R^3$, $R^{14}$ and $R^{15}$ together have the meanings given in one of rows 2 to 144 of table A.

Table 6:
Compounds of the formula Ia in which $R^2$ is difluoromethoxy and $R^{11}$, $R^{12}$$R^{13}$, $R^{14}$ and $R^{15}$ together have the meanings given in one of rows 2 to 144 of table A.

Table 7:
Compounds of the formula Ia in which $R^2$ is CN and $R^{11}$, $R^{12}$, $R^{13}$, $R^{14}$ and $R^{15}$ together have the meanings given in one of rows 2 to 144 of table A.

Table 8:
Compounds of the formula Ia in which $R^2$ is nitro and $R^{11}$, $R^{12}$, $R^{13}$, $R^{14}$ and $R^{15}$ together have the meanings given in one of rows 2 to 144 of table A.

Table 9:

Compounds of the formula Ia in which $R^2$ is OH and $R^{11}$, $R^{12}$, $R^{13}$, $R^{14}$ and $R^{15}$ together have the meanings given in one of rows 2 to 144 of table A.

A further particularly preferred embodiment of the invention is the compounds of the formula Ib

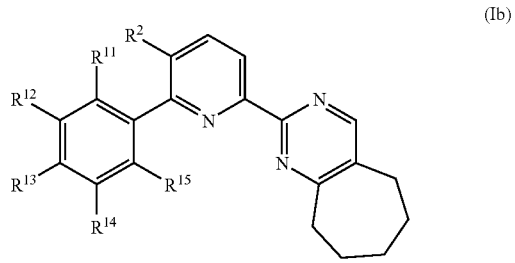

(Ib)

in which $R^{11}$, $R^{12}$, $R^{13}$, $R^{14}$ and $R^{15}$ have the meanings mentioned above and in particular the meanings mentioned as being preferred and $R^2$ has the meanings mentioned above and is in particular $C_1$-$C_4$-alkyl, especially methyl, ethyl, n-propyl, isopropyl, n-butyl, 2-butyl or tert-butyl, $C_1$-$C_4$-alkoxy, especially methoxy, ethoxy, isopropyloxy or tert-butyloxy, $C_1$-$C_2$-fluoroalkyl, especially trifluoromethyl or pentafluoroethyl, $C_1$-$C_2$-fluoroalkyloxy, especially difluoromethoxy or trifluoromethoxy, halogen, especially fluorine, chlorine or bromine, CN, $NO_2$ or OH. Examples of these compounds are the compounds of the formula Ib given in tables 10 to 30 below in which $R^{11}$, $R^{12}$, $R^{13}$, $R^{14}$ and $R^{15}$ together have the meanings given in one of rows 1 to 144 of table A.

Table 10:

Compounds of the formula Ib in which $R^2$ is methyl and $R^{11}$, $R^{12}$, $R^{13}$, $R^{14}$ and $R^{15}$ together have the meanings given in one of rows 1 to 144 of table A.

Table 11:

Compounds of the formula Ib in which $R^2$ is ethyl and $R^{11}$, $R^{12}$, $R^{13}$, $R^{14}$ and $R^{15}$ together have the meanings given in one of rows 1 to 144 of table A.

Table 12:

Compounds of the formula Ib in which $R^2$ is n-propyl and $R^{11}$, $R^{12}$, $R^{13}$, $R^{14}$ and $R^{15}$ together have the meanings given in one of rows 1 to 144 of table A.

Table 13:

Compounds of the formula Ib in which $R^2$ is isopropyl and $R^{11}$, $R^{12}$, $R^{13}$, $R^{14}$ and $R^{15}$ together have the meanings given in one of rows 1 to 144 of table A.

Table 14:

Compounds of the formula Ib in which $R^2$ is n-butyl and $R^{11}$, $R^{12}$, $R^{13}$, $R^{14}$ and $R^{15}$ together have the meanings given in one of rows 1 to 144 of table A.

Table 15:

Compounds of the formula Ib in which $R^2$ is 2-butyl and $R^{11}$, $R^{12}$, $R^{13}$, $R^{14}$ and $R^{15}$ together have the meanings given in one of rows 1 to 144 of table A.

Table 16:

Compounds of the formula Ib in which $R^2$ is tert-butyl and $R^{11}$, $R^{12}$, $R^{13}$, $R^{14}$ and $R^{15}$ together have the meanings given in one of rows 1 to 144 of table A.

Table 17:

Compounds of the formula Ib in which $R^2$ is methoxy and $R^{11}$, $R^{12}$, $R^{13}$, $R^{14}$ and $R^{15}$ together have the meanings given in one of rows 1 to 144 of table A.

Table 18:

Compounds of the formula Ib in which $R^2$ is ethoxy and $R^{11}$, $R^{12}$, $R^{13}$, $R^{14}$ and $R^{15}$ together have the meanings given in one of rows 1 to 144 of table A.

Table 19:

Compounds of the formula Ib in which $R^2$ is isopropyloxy and $R^{11}$, $R^{12}$, $R^{13}$, $R^{14}$ and $R^{15}$ together have the meanings given in one of rows 1 to 144 of table A.

Table 20:

Compounds of the formula Ib in which $R^2$ is tert-butyloxy and $R^{11}$, $R^{12}$, $R^{13}$, $R^{14}$ and $R^{15}$ together have the meanings given in one of rows 1 to 144 of table A.

Table 21:

Compounds of the formula Ib in which $R^2$ is trifluoromethoxy and $R^{11}$, $R^{12}$, $R^{13}$, $R^{14}$ and $R^{15}$ together have the meanings given in one of rows 1 to 144 of table A.

Table 22:

Compounds of the formula Ib in which $R^2$ is difluoromethoxy and $R^{11}$, $R^{12}$, $R^{13}$, $R^{14}$ and $R^{15}$ together have the meanings given in one of rows 1 to 144 of table A.

Table 23:

Compounds of the formula Ib in which $R^2$ is trifluoromethyl and $R^{11}$, $R^{12}$, $R^{13}$, $R^{14}$ and $R^{15}$ together have the meanings given in one of rows 1 to 144 of table A.

Table 24:

Compounds of the formula Ib in which $R^2$ is pentafluoroethyl and $R^{11}$, $R^{12}$, $R^{13}$, $R^{14}$ and $R^{15}$ together have the meanings given in one of rows 1 to 144 of table A.

Table 25:

Compounds of the formula Ib in which $R^2$ is fluorine and $R^{11}$, $R^{12}$, $R^{13}$, $R^{14}$ and $R^{15}$ together have the meanings given in one of rows 1 to 144 of table A.

Table 26:

Compounds of the formula Ib in which $R^2$ is chlorine and $R^{11}$, $R^{12}$, $R^{13}$, $R^{14}$ and $R^{15}$ together have the meanings given in one of rows 1 to 144 of table A.

Table 27:

Compounds of the formula Ib in which $R^2$ is bromine and $R^{11}$, $R^{12}$, $R^{13}$, $R^{14}$ and $R^{15}$ together have the meanings given in one of rows 1 to 144 of table A.

Table 28:

Compounds of the formula Ib in which $R^2$ is CN and $R^{11}$, $R^{12}$, $R^{13}$, $R^{14}$ and $R^{15}$ together have the meanings given in one of rows 1 to 144 of table A.

Table 29:

Compounds of the formula Ib in which $R^2$ is $NO_2$ and $R^{11}$, $R^{12}$, $R^{13}$, $R^{14}$ and $R^{15}$ together have the meanings given in one of rows 1 to 144 of table A.

Table 30:

Compounds of the formula Ib in which $R^2$ is OH and $R^{11}$, $R^{12}$, $R^{13}$, $R^{14}$ and $R^{15}$ together have the meanings given in one of rows 1 to 144 of table A.

A further particularly preferred embodiment of the invention is the compounds of the formula Ic (Ic)

(Ic)

in which $R^{11}$, $R^{12}$, $R^{13}$, $R^{14}$ and $R^{15}$ have the meanings mentioned above and in particular the meanings mentioned as being preferred and $R^2$ has the meanings mentioned above which are different from H and $C_1$-$C_4$-alkyl and is in particular $C_1$-$C_4$-alkoxy, especially methoxy, ethoxy, isopropyloxy, tert-butyloxy, $C_1$-$C_2$-fluoroalkyloxy, especially difluoromethoxy or trifluoromethoxy, CN, $NO_2$ or OH. Examples of these compounds are the compounds of the formula Ic given in tables 31 to 39 below in which $R^{11}$, $R^{12}$, $R^{13}$, $R^{14}$ and $R^{15}$ together have the meanings given in one of rows 2 to 144 of table A.

Table 31:
Compounds of the formula Ic in which $R^2$ is methoxy and $R^{11}$, $R^{12}$, $R^{13}$, $R^{14}$ and $R^{15}$ together have the meanings given in one of rows 2 to 144 of table A.

Table 32:
Compounds of the formula Ic in which $R^2$ is ethoxy and $R^{11}$, $R^{12}$, $R^{13}$, $R^{14}$ and $R^{15}$ together have the meanings given in one of rows 2 to 144 of table A.

Table 33:
Compounds of the formula Ic in which $R^2$ is isopropyloxy and $R^{11}$, $R^{12}$, $R^{13}$, $R^{14}$ and $R^{15}$ together have the meanings given in one of rows 2 to 144 of table A.

Table 34:
Compounds of the formula Ic in which $R^2$ is tert-butyloxy and $R^{11}$, $R^{12}$, $R^{13}$, $R^{14}$ and $R^{15}$ together have the meanings given in one of rows 2 to 144 of table A.

Table 35:
Compounds of the formula Ic in which $R^2$ is trifluoromethoxy and $R^{11}$, $R^{12}$, $R^{13}$, $R^{14}$ and $R^{15}$ together have the meanings given in one of rows 2 to 144 of table A.

Table 36:
Compounds of the formula Ic in which $R^2$ is difluoromethoxy and $R^{11}$, $R^{12}$, $R^{13}$, $R^{14}$ and $R^{15}$ together have the meanings given in one of rows 2 to 144 of table A.

Table 37:
Compounds of the formula Ic in which $R^2$ is CN and $R^{11}$, $R^{12}$, $R^{13}$, $R^{14}$ and $R^{15}$ together have the meanings given in one of rows 2 to 144 of table A.

Table 38:
Compounds of the formula Ic in which $R^2$ is nitro and $R^{11}$, $R^{12}$, $R^{13}$, $R^{14}$ and $R^{15}$ together have the meanings given in one of rows 2 to 144 of table A.

Table 39:
Compounds of the formula Ic in which $R^2$ is OH and $R^{11}$, $R^{12}$, $R^{13}$, $R^{14}$ and $R^{15}$ together have the meanings given in one of rows 2 to 144 of table A.

A further particularly preferred embodiment of the invention is the compounds of the formula Id (Id)

in which $R^{11}$, $R^{12}$, $R^{13}$, $R^{14}$ and $R^{15}$ have the meanings mentioned above and in particular the meanings mentioned as being preferred and $R^2$ has the meanings mentioned above and is in particular $C_1$-$C_4$-alkyl, especially methyl, ethyl, n-propyl, isopropyl, n-butyl, 2-butyl or tert-butyl, $C_1$-$C_4$-alkoxy, especially methoxy, ethoxy, isopropyloxy or tert-butyloxy, $C_1$-$C_2$-fluoroalkyl, especially trifluoromethyl or pentafluoroethyl, $C_1$-$C_2$-fluoroalkyloxy, especially difluoromethoxy or trifluoromethoxy, halogen, especially fluorine, chlorine or bromine, CN, $NO_2$ or OH. Examples of these compounds are the compounds of the formula Id given in tables 40 to 60 below in which $R^{11}$, $R^{12}$, $R^{13}$, $R^{14}$ and $R^{15}$ together have the meanings given in one of rows 1 to 144 of table A.

Table 40:
Compounds of the formula Id in which $R^2$ is methyl and $R^{11}$, $R^{12}$, $R^{13}$, $R^{14}$ and $R^{15}$ together have the meanings given in one of rows 1 to 144 of table A.

Table 41:
Compounds of the formula Id in which $R^2$ is ethyl and $R^{11}$, $R^{12}$, $R^{13}$, $R^{14}$ and $R^{15}$ together have the meanings given in one of rows 1 to 144 of table A.

Table 42:
Compounds of the formula Id in which $R^2$ is n-propyl and $R^{11}$, $R^{12}$, $R^{13}$, $R^{14}$ and $R^{15}$ together have the meanings given in one of rows 1 to 144 of table A.

Table 43:
Compounds of the formula Id in which $R^2$ is isopropyl and $R^{11}$, $R^{12}$, $R^{13}$, $R^{14}$ and $R^{15}$ together have the meanings given in one of rows 1 to 144 of table A.

Table 44:
Compounds of the formula Id in which $R^2$ is n-butyl and $R^{11}$, $R^{12}$, $R^{13}$, $R^4$ and $R^5$ together have the meanings given in one of rows 1 to 144 of table A.

Table 45:
Compounds of the formula Id in which $R^2$ is 2-butyl and $R^{11}$, $R^{12}$, $R^{13}$, $R^{14}$ and $R^{15}$ together have the meanings given in one of rows 1 to 144 of table A.

Table 46:
Compounds of the formula Id in which $R^2$ is tert-butyl and $R^{11}$, $R^{12}$, $R^{13}$, $R^{14}$ and $R^{15}$ together have the meanings given in one of rows 1 to 144 of table A.

Table 47:
Compounds of the formula Id in which $R^2$ is methoxy and $R^{11}$, $R^{12}$, $R^{13}$, $R^{14}$ and $R^{15}$ together have the meanings given in one of rows 1 to 144 of table A.

Table 48:
Compounds of the formula Id in which $R^2$ is ethoxy and $R^{11}$, $R^{12}$, $R^{13}$, $R^{14}$ and $R^{15}$ together have the meanings given in one of rows 1 to 144 of table A.

Table 49:
Compounds of the formula Id in which $R^2$ is isopropyloxy and $R^{11}$, $R^{12}$, $R^{13}$, $R^{14}$ and $R^{15}$ together have the meanings given in one of rows 1 to 144 of table A.

Table 50:
Compounds of the formula Id in which $R^2$ is tert-butyloxy and $R^{11}$, $R^{12}$, $R^{13}$, $R^{14}$ and $R^{15}$ together have the meanings given in one of rows 1 to 144 of table A.

Table 51:
Compounds of the formula Id in which $R^2$ is trifluoromethoxy and $R^{11}$, $R^{12}$, $R^{13}$, $R^{14}$ and $R^{15}$ together have the meanings given in one of rows 1 to 144 of table A.

Table 52:
Compounds of the formula Id in which $R^2$ is difluoromethoxy and $R^{11}$, $R^{12}$, $R^{13}$, $R^{14}$ and $R^{15}$ together have the meanings given in one of rows 1 to 144 of table A.

Table 53:
Compounds of the formula Id in which $R^2$ is trifluoromethyl and $R^{11}$, $R^{12}$, $R^{13}$, $R^{14}$ and $R^{15}$ together have the meanings given in one of rows 1 to 144 of table A.

Table 54:
Compounds of the formula Id in which $R^2$ is pentafluoroethyl and $R^{11}$, $R^{12}$, $R^{13}$, $R^{14}$ and $R^{15}$ together have the meanings given in one of rows 1 to 144 of table A.

Table 55:
Compounds of the formula Id in which $R^2$ is fluorine and $R^{11}$, $R^{12}$, $R^{13}$, $R^{14}$ and $R^{15}$ together have the meanings given in one of rows 1 to 144 of table A.

Table 56:
Compounds of the formula Id in which $R^2$ is chlorine and $R^{11}$, $R^{12}$, $R^{13}$, $R^{14}$ and $R^{15}$ together have the meanings given in one of rows 1 to 144 of table A.

Table 57:
Compounds of the formula Id in which $R^2$ is bromine and $R^{11}$, $R^{12}$, $R^{13}$, $R^{14}$ and $R^{15}$ together have the meanings given in one of rows 1 to 144 of table A.

Table 58:
Compounds of the formula Id in which $R^2$ is CN and $R^{11}$, $R^{12}$, $R^{13}$, $R^{14}$ and $R^{15}$ together have the meanings given in one of rows 1 to 144 of table A.

Table 59:
Compounds of the formula Id in which $R^2$ is $NO_2$ and $R^{11}$, $R^{12}$, $R^{13}$, $R^{14}$ and $R^{15}$ together have the meanings given in one of rows 1 to 144 of table A.

Table 60:
Compounds of the formula Id in which $R^2$ is OH and $R^{11}$, $R^{12}$, $R^{13}$, $R^{14}$ and $R^{15}$ together have the meanings given in one of rows 1 to 144 of table A.

A further preferred embodiment of the invention is the compounds of the formula Ie, (Ie)

in which $R^{11}$, $R^{12}$, $R^{13}$, $R^{14}$ and $R^{15}$ have the meanings mentioned above and in particular the meanings mentioned as being preferred and $R^2$ has the meanings mentioned above and is in particular $C_1$-$C_4$-alkyl, especially methyl, ethyl, n-propyl, isopropyl, n-butyl, 2-butyl or tert-butyl, $C_1$-$C_4$-alkoxy, especially methoxy, ethoxy, isopropyloxy or tert-butyloxy, $C_1$-$C_2$-fluoroalkyl, especially trifluoromethyl or pentafluoroethyl, $C_1$-$C_2$-fluoroalkyloxy, especially difluoromethoxy or trifluoromethoxy, halogen, especially fluorine, chlorine or bromine, CN, $NO_2$ or OH. Examples of these compounds are the compounds of the formula Ie given in tables 61 to 81 below in which $R^{11}$, $R^{12}$, $R^{13}$, $R^{14}$ and $R^{15}$ together have the meanings given in one of rows 1 to 144 of table A.

Table 61:
Compounds of the formula Ie in which $R^2$ is methyl and $R^{11}$, $R^{12}$, $R^{13}$, $R^{14}$ and $R^{15}$ together have the meanings given in one of rows 1 to 144 of table A.

Table 62:
Compounds of the formula Ie in which $R^2$ is ethyl and $R^{11}$, $R^{12}$, $R^{13}$, $R^{14}$ and $R^{15}$ together have the meanings given in one of rows 1 to 144 of table A.

Table 63:
Compounds of the formula Ie in which $R^2$ is n-propyl and $R^{11}$, $R^{12}$, $R^{13}$, $R^{14}$ and $R^{15}$ together have the meanings given in one of rows 1 to 144 of table A.

Table 64:
Compounds of the formula Ie in which $R^2$ is isopropyl and $R^{11}$, $R^{12}$, $R^{13}$, $R^{14}$ and $R^{15}$ together have the meanings given in one of rows 1 to 144 of table A.

Table 65:
Compounds of the formula Ie in which $R^2$ is n-butyl and $R^{11}$, $R^{12}$, $R^{13}$, $R^{14}$ and $R^{15}$ together have the meanings given in one of rows 1 to 144 of table A.

Table 66:
Compounds of the formula Ie in which $R^2$ is 2-butyl and $R^{11}$, $R^{12}$, $R^{13}$, $R^{14}$ and $R^{15}$ together have the meanings given in one of rows 1 to 144 of table A.

Table 67:
Compounds of the formula Ie in which $R^2$ is tert-butyl and $R^{11}$, $R^{12}$, $R^{13}$, $R^{14}$ and $R^{15}$ together have the meanings given in one of rows 1 to 144 of table A.

Table 68:
Compounds of the formula Ie in which $R^2$ is methoxy and $R^{11}$, $R^{12}$, $R^{13}$, $R^{14}$ and $R^{15}$ together have the meanings given in one of rows 1 to 144 of table A.

Table 69:

Compounds of the formula Ie in which $R^2$ is ethoxy and $R^{11}$, $R^{12}$, $R^{13}$, $R^{14}$ and $R^{15}$ together have the meanings given in one of rows 1 to 144 of table A.

Table 70:

Compounds of the formula Ie in which $R^2$ is isopropyloxy and $R^{11}$, $R^{12}$, $R^{13}$, $R^{14}$ and $R^{15}$ together have the meanings given in one of rows 1 to 144 of table A.

Table 71:

Compounds of the formula Ie in which $R^2$ is tert-butyloxy and $R^{11}$, $R^{12}$, $R^{13}$, $R^{14}$ and $R^{15}$ together have the meanings given in one of rows 1 to 144 of table A.

Table 72:

Compounds of the formula Ie in which $R^2$ is trifluoromethoxy and $R^{11}$, $R^{12}$, $R^{13}$, $R^{14}$ and $R^{15}$ together have the meanings given in one of rows 1 to 144 of table A.

Table 73:

Compounds of the formula Ie in which $R^2$ is difluoromethoxy and $R^{11}$, $R^{12}$, $R^{13}$, $R^{14}$ and $R^{15}$ together have the meanings given in one of rows 1 to 144 of table A.

Table 74:

Compounds of the formula Ie in which $R^2$ is trifluoromethyl and $R^{11}$, $R^{12}$, $R^{13}$, $R^{14}$ and $R^{15}$ together have the meanings given in one of rows 1 to 144 of table A.

Table 75:

Compounds of the formula Ie in which $R^2$ is pentafluoroethyl and $R^{11}$, $R^{12}$, $R^{13}$, $R^{14}$ and $R^{15}$ together have the meanings given in one of rows 1 to 144 of table A.

Table 76:

Compounds of the formula Ie in which $R^2$ is fluorine and $R^{11}$, $R^{12}$, $R^{13}$, $R^{14}$ and $R^{15}$ together have the meanings given in one of rows 1 to 144 of table A.

Table 77:

Compounds of the formula Ie in which $R^2$ is chlorine and $R^{11}$, $R^{12}$, $R^{13}$, $R^{14}$ and $R^{15}$ together have the meanings given in one of rows 1 to 144 of table A.

Table 78:

Compounds of the formula Ie in which $R^2$ is bromine and $R^{11}$, $R^{12}$, $R^{13}$, $R^{14}$ and $R^{15}$ together have the meanings given in one of rows 1 to 144 of table A.

Table 79:

Compounds of the formula Ie in which $R^2$ is CN and $R^{11}$, $R^{12}$, $R^{13}$, $R^{14}$ and $R^{15}$ together have the meanings given in one of rows 1 to 144 of table A.

Table 80:

Compounds of the formula Ie in which $R^2$ is $NO_2$ and $R^{11}$, $R^{12}$, $R^{13}$, $R^{14}$ and $R^{15}$ together have the meanings given in one of rows 1 to 144 of table A.

Table 81:

Compounds of the formula Ie in which $R^2$ is OH and $R^{11}$, $R^{12}$, $R^{13}$, $R^{14}$ and $R^{15}$ together have the meanings given in one of rows 1 to 144 of table A.

The compounds of the formula I according to the invention can be prepared, for example, according to the process shown in scheme 1:

Scheme 1:

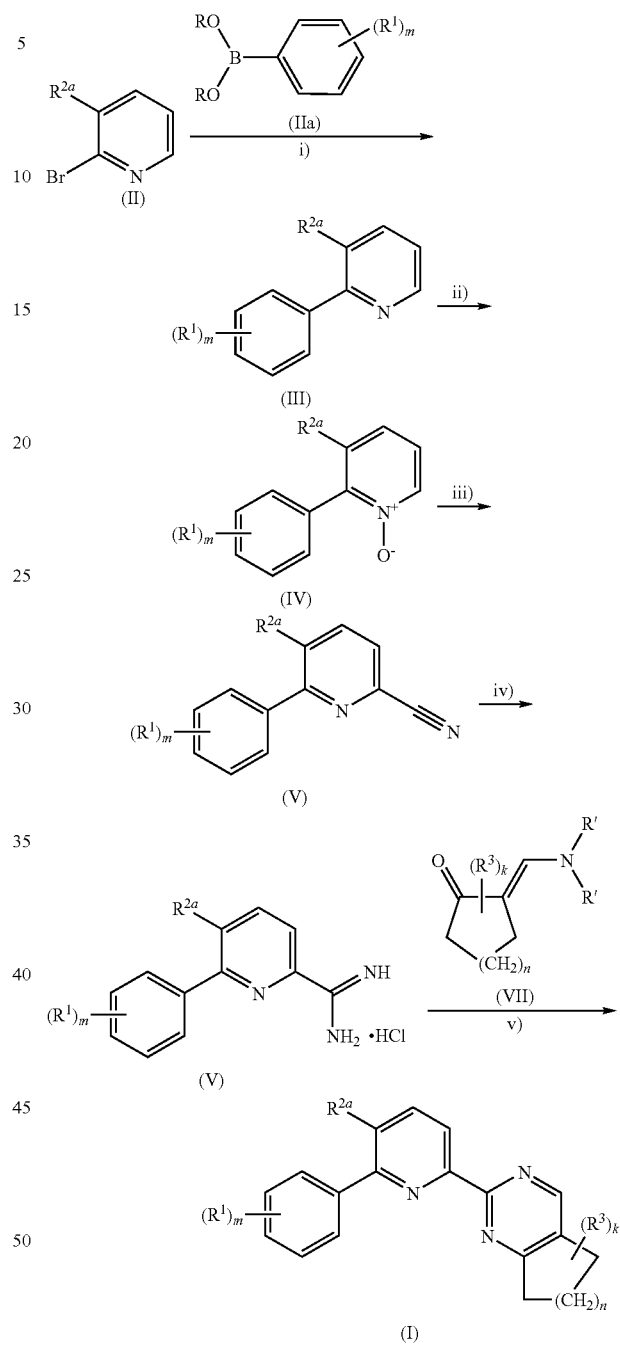

In scheme 1, $R^1$, $R^3$, m, n and k are as defined above. $R^{2a}$ is H, $C_1$-$C_4$-alkyl, $C_1$-$C_4$-haloalkyl, halogen, $C_1$-$C_4$-alkoxy, $C_1$-$C_4$-haloalkoxy, $NO_2$ or OH. R is H or $C_1$-$C_4$-alkyl or, together with further molecules IIa, forms a phenylboronic acid anhydride. $R^1$ is $C_1$-$C_4$-alkyl and in particular methyl.

In a first step i), a 2-bromopyridine is reacted with a phenylboronic acid derivative of the formula IIa under the conditions of a Suzuki coupling, i.e. in the presence of a platinum metal catalyst and in particular in the presence of a palladium catalyst, under reaction conditions known per se, as known, for example, from Acc. Chem. Res. 15 (1982), 178-184, Chem. Rev. 95 (1995), 2457-2483 and the literature cited therein, and also from J. Org. Chem. 68 (2003), 9412. Suitable catalysts are in particular tetrakis(triphenylphosphine) palladium (0), bis(triphenylphosphine) palladium (II) chloride, bis(acetonitrile)palladium (II) chloride, [1,1'-bis(diphenylphosphine) ferrocene]-palladium (II) chloride/dichloromethane complex, bis[1,2-bis(diphenylphosphine)-ethane] palladium(0) and [1,4-bis(diphenylphosphine)butane] palladium(II) chloride. The amount of catalyst is usually from 0.1 to 10 mol %.

The resulting 2-phenylpyridine of the formula III is subsequently, in step ii), converted by treatment with a peracid under conditions known per se into the 2-phenylpyridine N-oxide of the formula IV. The conversion of III into IV can be carried out analogously to known processes, for example by treating III with hydrogen peroxide in an organic acid, such as formic acid, acetic acid, chloroacetic acid or trifluoroacetic acid (see, for example, J. Org. Chem. 55 (1990), 738-741 and Organic Synthesis, Collect. Vol. IV (1963), 655-656), or by reacting III with an organic peracid, such as meta-perchlorobenzoic acid, in an inert solvent, for example a halogenated hydrocarbon, such as dichloromethane or dichloroethane (see, for example, Synthetic Commun. 22 (18) (1992), 2645; J. Med. Chem. (1998), 2146). The conversion of III into IV can also be achieved analogously to the method described by K. B. Scharpless (J. Org. Chem. 63 (5) (1998), 7740) by reacting III with hydrogen peroxide in a halogenated hydrocarbon, such as dichloromethane or dichloroethane, in the presence of catalytic amounts (for example 5% by weight) of rhenium(VII) compounds, such as methyltrioxorhenium ($H_3CReO_3$).

The conversion of the 2-phenylpyridine N-oxide of the formula IV into the nitrile V in step iii) can be carried out, for example, by a modified Reissert-Henze reaction analogously to the methods described in J. Org. Chem. 48 (1983), 1375 and J. Org. Chem. 55 (1990), 738-741, by reacting IV with a trialkylsilyl cyanide, such as trimethylsilyl cyanide, in the presence of N,N-dimethylchloroformamide. Alternatively, the nitrile V can be prepared from the 2-phenylpyridine N-oxide IV by successive reaction with dimethyl sulfate and then with cyanide ions, for example with sodium cyanide or potassium cyanide, analogously to the method described in Tetrahedron (1985), 4947.

The 2-cyano-6-phenylpyridine compound, obtained in step iii), of the formula V is then, in step iv), converted by the method described in U.S. Pat. No. 4,873,248 into the amidinium hydrochloride of the formula VI. The conversion is carried out by successive treatment with alkali metal alkoxide, such as sodium methoxide or sodium ethoxide, and subsequent reaction with ammonium chloride. Instead of the hydrochlorides, it is also possible to use the hydrobromides, acetates, sulfates or formates in the subsequent step v).

The resulting amidinium hydrochloride of the formula VI is then, in step v), reacted with a dialkylaminomethylenecycloalkanone of the formula VII (enamino ketone VII) in the presence of a base, preferably an alkali metal alkoxide, such as sodium methoxide or sodium ethoxide. The reaction can be carried out analogously to known processes for reacting amidinium hydrochlorides with enamino ketones, as described, for example, in J. Heterocycl. Chem. 20 (1983), 649-653.

Instead of the enamino ketones VII, it is also possible to use, in step v), β-oxoacetals of the formula VIIIa

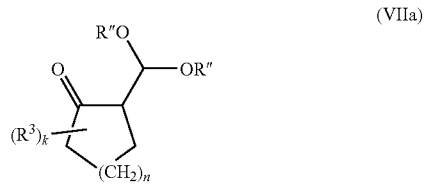

In formula VIIa, R" is $C_1$-$C_4$-alkyl and in particular methyl or ethyl. The reaction of VI with VIIa can be carried out analogously to the method (a) described in EP-A 259139, which is incorporated herein by way of reference.

Dialkylaminomethylenecycloalkanones of the formula VII are known or can be prepared analogously to known methods (see, for example, WO 2001/087845, Tetrahedron 50(7) (1994), 2255-2264; Synthetic Communications 28(10) (1998), 1743-1753 or Tetrahedron Letters 27(23) (1986), 2567-70). β-Oxoacetals of the formula VIIIa are likewise known, for example from EP 259139, or can be obtained commercially.

Alternatively, the compounds of the formula I can be prepared by the synthesis route shown in Scheme 2:

Scheme 2:

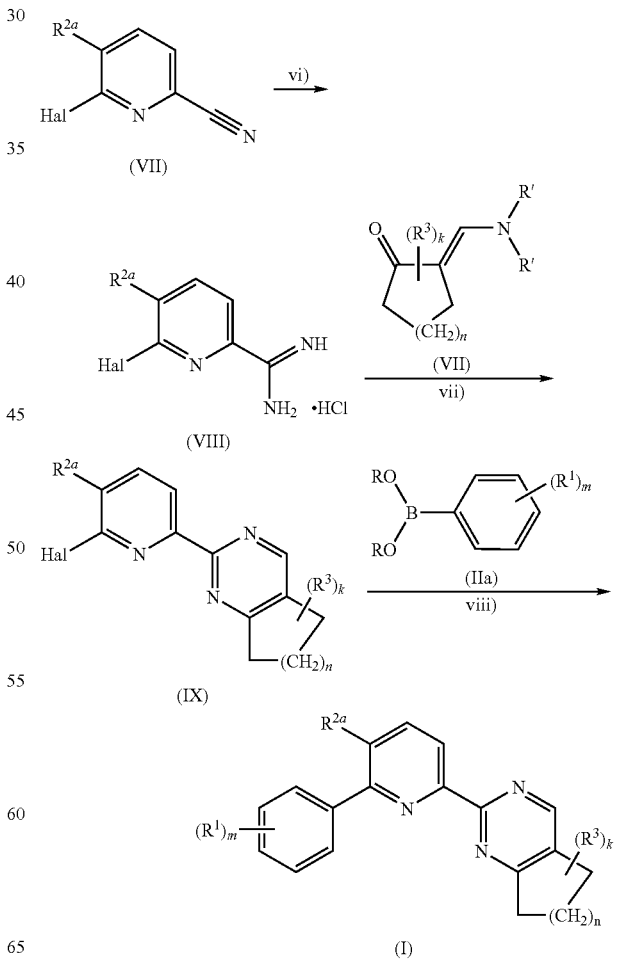

In Scheme 2, R, R', $R^1$, $R^3$, m, n and k are as defined above. $R^{2a}$ is H, $C_1$-$C_4$-alkyl or $C_1$-$C_4$-haloalkyl. Hal is bromine or chlorine.

With respect to the reaction conditions for step vi), what was said for step iv) in Scheme 1 applies. With respect to the reaction conditions for step vii), what was said for step v) in Scheme 1 applies. With respect to the reaction conditions for step viii), what was said for step i) in Scheme 1 applies. Cyanopyridines of the formula VII are known, for example from US 2003/087940, WO 2004/026305, WO 01/057046 and Bioorg. Med. Chem. Lett. (2003), 1571-1574, or they can be prepared by known preparation processes.

Compounds of the formula VII can be prepared, in particular, by the process shown in scheme 3.

formula V which are then, according to steps iv) and v) of Scheme 1, converted into the compound of the formula I according to the invention.

Instead of the boronic acid (derivatives) IIa, it is also possible to use phenyl-Grignard compounds of the formula IIb in Scheme 1, step i), Scheme 2, step viii) and Scheme 3, step xii).

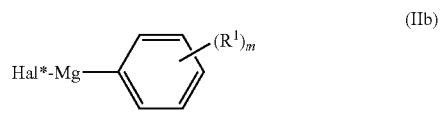

Scheme 3:

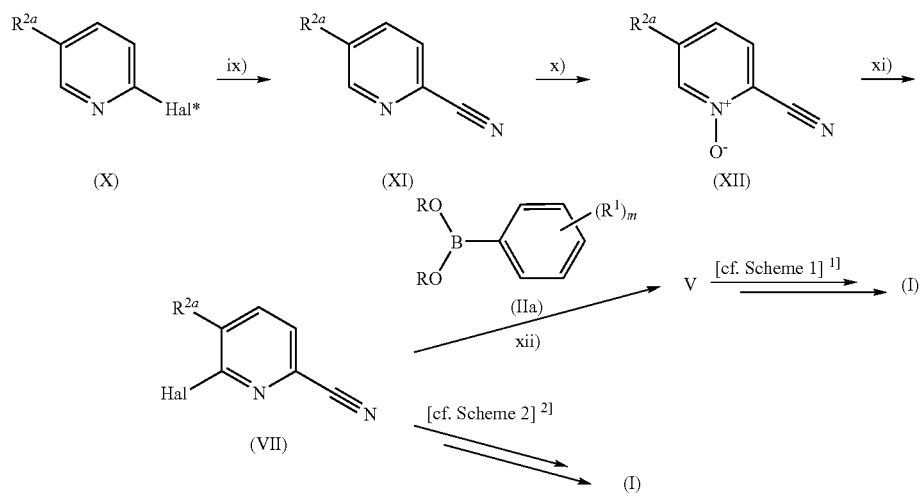

In Scheme 3, R, $R^1$ and m are as defined above. $R^{2a}$ is $C_1$-$C_4$-alkyl, $C_1$-$C_4$-haloalkyl, halogen, $C_1$-$C_4$-alkoxy, $C_1$-$C_4$-haloalkoxy or $NO_2$. Hal and Hal* independently of one another are chlorine or bromine, where Hal* may also be iodine.

The conversion of the 2-halopyridine X into the 2-cyanopyridine XI in step ix) is achieved by standard methods of organic chemistry by reacting X with cyanide ions, for example with sodium cyanide or potassium cyanide (see EP-A 97460, preparation example 1), copper(I) cyanide (see EP-A 34917, preparation example 3) or tetramethylsilyl cyanide. The resulting compound XI is subsequently, analogously to the methods illustrated in Scheme 1, step ii), converted into the pyridine N-oxide XII (step x). XII is subsequently, in step xi), reacted with a halogenating agent, such as $POCl_3$ or $POBr_3$, which gives the corresponding compound VII. For reacting XII in step ix), the halogenating agent is generally employed in excess, based on the stoichiometry of the reaction. The reaction can be carried out in an inert organic solvent and is frequently carried out in the absence of a solvent, in which case the halogenating agent then generally acts as solvent. The reaction temperature is usually in the range from 20° C. to the boiling point of the halogenating agent. The compound VII can subsequently, by the method shown in Scheme 2, be converted into the compound I. Alternatively, the compound VII can initially be reacted with phenylboronic acid, by the methods mentioned in Scheme 1, step i) or Scheme 2, step viii), which gives the compounds of the In formula IIb, $R^1$ and m are as defined above. Hal* is chlorine, bromine or iodine. The coupling reaction in Scheme 1, step i), Scheme 2, step viii) and Scheme 3, step xii) is then carried out in the presence of the palladium catalysts mentioned above or in the presence of tris(acetylacetonato)iron (III) (see Tetrahedron Lett. (2002), 3547), under, if appropriate, slightly modified conditions, where the catalyst is usually employed in an amount of from 0.2 to 8 mol %, in particular 0.5 to 5 mol %, based on the Grignard compound IIb to be coupled. The particularly preferred catalyst is [1,4-bis(diphenyl-phosphine)butane]palladium(II) chloride. The reactions are generally carried out at temperatures in the range from –40 to +120° C. and in particular in the range from 20 to 100° C. The reactions are usually carried out in an inert aprotic organic solvent, preferably an ether and in particular a cyclic ether, such as tetrahydrofuran, or in a mixture of different aprotic inert solvents, where preferably one of the solvents is a cyclic ether, such as tetrahydrofuran. Examples of such mixtures are tetrahydrofuran/N-methylpyrrolidone, tetrahydrofuran/toluene or xylene, tetrahydrofuran/dioxane, tetrahydrofuran/N,N-dimethylpropyleneurea (DMPU) and also tetrahydrofuran/sulfolane.

A further route to the compounds of the formula I where $R^2$=H, alkyl, alkoxy or in particular CN is illustrated in Scheme 4.

Scheme 4:

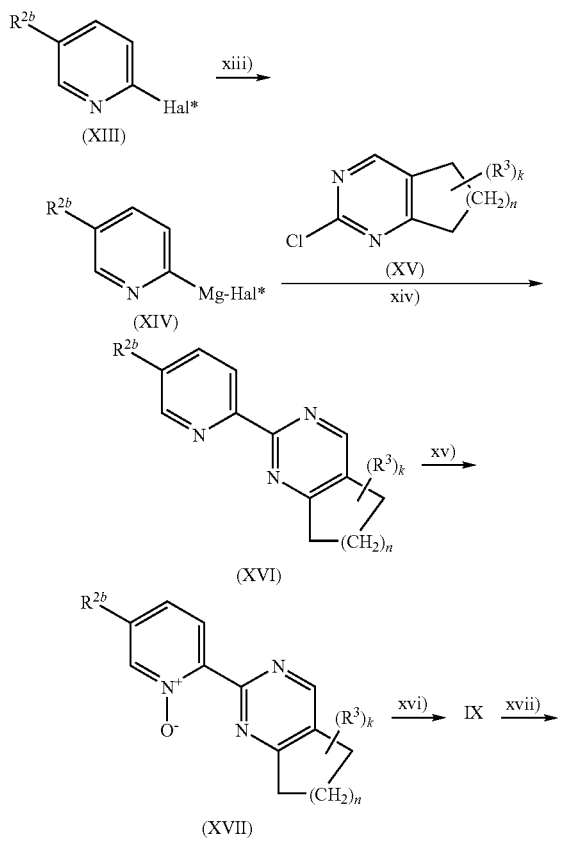

In Scheme 4, n, $R^3$ and k are as defined above. $R^{2b}$ is H, $C_1$-$C_4$-alkyl or $C_1$-$C_4$-alkoxy and in particular CN. Hal* is chlorine, bromine or, in particular, iodine. The preparation of the Grignard compound XIV from the 2-halopyridine XIII can be carried out by processes known per se, as described, for example, in Synlett (1998), 1359.

The subsequent coupling of XIV with the 2-chloropyrimidine compound XV in step xiv) is carried out analogously to the coupling of Grignard compounds IIb already illustrated. The coupling is preferably carried out in the presence of a transition metal catalyst of a metal of group 8 to 10 (according to IUPAC 1989), in particular a palladium, nickel or iron catalyst. With respect to the catalyst, reference is made to the catalysts mentioned above. The reaction is carried out in a solvent customary for this purpose, for example an ether, such as diethyl ether, dioxane, tetrahydrofuran, an aromatic hydrocarbon, such as toluene or xylenes, or an aprotic amide, lactam or urea, such as N-methylpyrrolidone or dimethylpropyleneurea, or in mixtures of these solvents, in particular mixtures comprising at least one ether. The reaction temperatures are generally in the range from −40 to +120° C. and in particular in the range from 20 to 100° C. For further details, reference is made to the methods described in J. Am. Chem. Soc. 124 (2002), 13856, Chem. Pharm. Bull. (1983), 4533 and Chem. Pharm. Bull. (1984), 2005, which can be used in an analogous manner for coupling XIV with XV.

The resulting compound XVI is then, in step xv), converted into the N-oxide XVII. With respect to step xv), reference is made to what was said for step ii) in Scheme 1 or step x) in Scheme 3. Subsequently, in step xvi), the N-oxide XVII is, analogously to step xi) in Scheme 3, reacted with a halogenating agent, such as $POCl_3$ or $POBr_3$, which gives the 2-halo compound IX from Scheme 2. This compound is then, by the method illustrated in Scheme 2, step viii), reacted with a phenylboronic acid compound IIa or the corresponding Grignard compound IIb, which gives the compound of the formula I.

Compounds of the formula XV are known or can be prepared by methods, known per se, of organic chemistry (see, for example, U.S. Pat. No. 6,040,448, WO 99/21850 and Chem. Pharm. Bull (1983), 2254).

The reaction mixtures obtained by the methods illustrated in Schemes 1 to 4 are worked up in the customary manner, for example by mixing with water, separating the phases and, if appropriate, chromatographic purification of the crude products. Some of the intermediates and end products are obtained in the form of colorless or slightly brownish viscous oils which can be purified or freed from volatile components under reduced pressure and at moderately elevated temperature. If the intermediates and end products are obtained as solids, purification can also be carried out by recrystallization or digestion.

If individual compounds I cannot be obtained by the routes described above, they can be prepared by derivatization of other compounds I.

If the synthesis yields mixtures of isomers, a separation is generally not necessarily required since in some cases the individual isomers can be interconverted during work-up for use or during application (for example under the action of light, acids or bases). Such conversions may also take place after use, for example in the treatment of plants in the treated plant, or in the harmful fungus to be controlled.

The compounds I are suitable as fungicides. They are distinguished by an outstanding effectiveness against a broad spectrum of phytopathogenic fungi, especially from the classes of the *Ascomycetes*, *Deuteromycetes*, *Oomycetes* and *Basidiomycetes*. Some are systemically effective and they can be used in plant protection as foliar and soil fungicides.

They are particularly important in the control of a multitude of fungi on various cultivated plants, such as wheat, rye, barley, oats, rice, maize, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

*Alternaria* species on fruit and vegetables,
*Bipolaris*- and *Drechslera* species on cereals, rice and lawns,
*Blumeria graminis* (powdery mildew) on cereals,
*Botrytis cinerea* (gray mold) on strawberries, vegetables, ornamental plants and grapevines,
*Erysiphe cichoracearum* and *Sphaerotheca fuliginea* on cucumbers,
*Fusarium* and *Verticillium* species on various plants,
*Mycosphaerella* species on cereals, bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria tritici* and *Stagnospora nodorum* on wheat,
*Uncinula necator* on grapevines,
*Ustilago* species on cereals and sugar cane, and
*Venturia* species (scab) on apples and pears.

The compounds I are also suitable for controlling harmful fungi, such as *Paecilomyces variotii*, in the protection of materials (e.g. wood, paper, paint dispersions, fibers or fabrics) and in the protection of stored products.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally required.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

The compounds I can be converted into the customary formulations, for example solutions, emulsions, suspensions, dusts, powders, pastes and granules. The application form depends on the particular purpose; in each case, it should ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable are essentially:

water, aromatic solvents (for example Solvesso products, xylene), paraffins (for example mineral fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

Examples of formulations include products for dilution with water, for example

A water-soluble concentrates (SL)

10 parts by weight of a compound according to the invention are dissolved in water or in a water-soluble solvent. As an alternative, wetters or other auxiliaries are added. The active compound dissolves upon dilution with water;

B dispersible concentrates (DC)

20 parts by, weight of a compound according to the invention are dissolved in cyclohexanone with addition of a dispersant, for example polyvinylpyrrolidone. Dilution with water gives a dispersion;

C emulsifiable concentrates (EC)

15 parts by weight of a compound according to the invention are dissolved in xylene with addition of calcium dodecylbenzenesulfonate and castor oil ethoxylate (in each case 5%). Dilution with water gives an emulsion;

D emulsions (EW, EO)

40 parts by weight of a compound according to the invention are dissolved in xylene with addition of calcium dodecylbenzenesulfonate and castor oil ethoxylate (in each case 5%). This mixture is introduced into water by means of an emulsifying machine (Ultraturax) and made into a homogeneous emulsion. Dilution with water gives an emulsion;

E suspensions (SC, OD)

In an agitated ball mill, 20 parts by weight of a compound according to the invention are comminuted with addition of dispersants, wetters and water or an organic solvent to give a fine active compound suspension. Dilution with water gives a stable suspension of the active compound;

F water-dispersible granules and water-soluble granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active compound;

G water-dispersible powders and water-soluble powders (WP, SP)

75 parts by weight of a compound according to the invention are ground in a rotor-stator mill with addition of dispersants, wetters and silica gel. Dilution with water gives a stable dispersion or solution of the active compound;

and also products to be applied undiluted, for example

H dustable powders (DP)

5 parts by weight of a compound according to the invention are ground finely and mixed intimately with 95% of finely divided kaolin. This gives a dustable product;

I granules (GR, FG, GG, MG)

0.5 part by weight of a compound according to the invention is ground finely and associated with 95.5% carriers. Current methods are extrusion, spray-drying or the fluidized bed. This gives granules to be applied undiluted;

J ULV solutions (UL)

10 parts by weight of a compound according to the invention are dissolved in an organic solvent, for example xylene. This gives a product to be applied undiluted.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; the intention is to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), by which it is possible to apply formulations comprising over 95% by weight of active compound, or even to apply the active compound without additives.

Various types of oils, wetters, adjuvants, herbicides, fungicides, other pesticides, or bactericides may be added to the active compounds, if appropriate not until immediately prior to use (tank mix). These agents can be admixed with the agents according to the invention in a weight ratio of 1:10 to 10:1.

The compositions according to the invention can, in the use form as fungicides, also be present together with other active compounds, e.g. with herbicides, insecticides, growth regulators, fungicides or else with fertilizers. Mixing the compounds I or the compositions comprising them in the application form as fungicides with other fungicides results in many cases in an expansion of the fungicidal spectrum of activity being obtained.

The following list of fungicides, with which the compounds according to the invention can be used in conjunction, is intended to illustrate the possible combinations but does not limit them:

acylalanines, such as benalaxyl, metalaxyl, ofurace, oxadixyl, amine derivatives, such as aldimorph, dodine, dodemorph, fenpropimorph, fenpropidin, guazatine, iminoctadine, spiroxamine, tridemorph, anilinopyrimidines, such as pyrimethanil, mepanipyrim or cyprodinyl, antibiotics, such as cycloheximide, griseofulvin, kasugamycin, natamycin, polyoxin or streptomycin, azoles, such as bitertanol, bromoconazole, cyproconazole, difenoconazole, dinitroconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, triflumizole, triticonazole, dicarboximides, such as iprodione, myclozolin, procymidone, vinclozolin, dithiocarbamates, such as ferbam, nabam, maneb, mancozeb, metam, metiram, propineb, polycarbamate, thiram, ziram, zineb, heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole, triforine, copper fungicides, such as Bordeaux mixture, copper acetate, copper oxychloride, basic copper sulfate, nitrophenyl derivatives, such as binapacryl, dinocap, dinobuton, nitrophthal-isopropyl, phenylpyrroles, such as fenpiclonil or fludioxonil, sulfur, other fungicides, such as acibenzolar-S-methyl, benthiavalicarb, carpropamid, chlorothalonil, cyflufenamid, cymoxanil, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene, zoxamide, strobilurins, such as azoxystrobin, dimoxystrobin, fluoxastrobin, kresoxim-methyl, metominostrobin, orysastrobin, picoxystrobin, pyraclostrobin or trifloxystrobin, sulfenic acid derivatives, such as captafol, captan, dichlofluanid, folpet, tolylfluanid, cinnamides and analogous compounds, such as dimethomorph, flumetover or flumorph.

SYNTHESIS EXAMPLES

The procedures described in the synthesis examples below were used to prepare further compounds by appropriate modification of the starting compounds. The compounds thus obtained are listed in the tables below, together with physical data.

The following abbreviations are used in the examples:
m.p.: melting point;
MtBE: methyl tert-butyl ether;
EtOH: ethanol.

The following abbreviations are used in connection with the $^1$H-NMR data:
s: singlet; d: doublet; t: triplet; m: multiplet

Example 1

2-(5-methyl-6-phenylpyridin-2-yl)-6,7,8,9-tetrahydro-5H-cycloheptapyrimidine

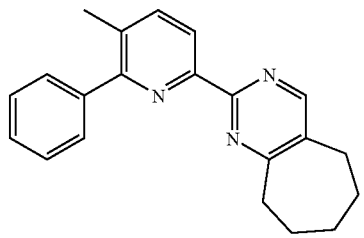

1.1 3-methyl-2-phenylpyridine 2.1 g (17.2 mmol) of phenylboronic acid and 4.3 g of potassium carbonate in 20 ml of water were added successively to a solution of 2.0 g (11.6 mmol) of 2-bromo-3-methylpyridine in 80 ml of tetrahydrofuran. After addition of 300 mg of tetrakis(triphenylphosphine)palladium(0), the mixture was stirred under reflux for 8 hours. The reaction solution was poured into ice-water and extracted with MtBE. The combined organic phases were dried, the solvent was removed under reduced pressure and the residue was chromatographed on silica gel using cyclohexane/MtBE (9:1). This gave 0.8 g of product.

$^1$H-NMR (δ, CDCl$_3$,): 2.5 (s); 7.2 (m); 7.35-7.6 (m) and 8.5 (m)

1.2 3-methyl-2-phenylpyridine N-oxide 25 g (147.7 mmol) of 3-methyl-2-phenylpyridine were initially charged in 150 ml of dichloromethane. At 5° C., 51.6 g (294 mmol) of 3-chloroperoxybenzoic acid was added a little at a time, and the mixture was stirred at 5° C. for 2 hours and at 23° C. for 18 hours. The solvent was removed and the residue was then chromatographed on silica gel using cyclohexane/MtBE (1:1), which gave 25 g of product.
m.p.: 163-165° C.
$^1$H-NMR (δ, CDCl$_3$,): 2.0 (s); 7.1-7.6 (m); 8.3 (m).

1.3 5-methyl-6-phenylpyridine-2-carbonitrile 14.9 g (150 mmol) of trimethylsilyl cyanide were added to a solution of 25 g (118.2 mmol) of the compound prepared in example 1.2 in 150 ml of dichloromethane, and the mixture was stirred at room temperature for 30 minutes. A solution of 16.2 g (150 mmol) of dimethylcarbamoyl chloride was then added over a period of 45 min, and the mixture was stirred at 23° C. for 18 hours. 70 ml of water and 40 ml of 1 N aqueous sodium hydroxide solution were carefully added to the reaction solution. The pH was then adjusted to 8 using solid sodium carbonate. The organic phase was separated off, washed with water and dried. Removal of the solvent gave, after chromatography on silica gel using cyclohexane/MtBE (3:2), 19.9 g of the title compound as an oil.
$^1$H-NMR (δ, CDCl$_3$,): 2.45 (s); 7.4-7.8 (m)

1.4 5-methyl-6-phenylpyridine-2-carboxamidine hydrochloride 2.34 g of a 30% strength solution of sodium methoxide in methanol were added to a solution of 5.0 g (26 mmol) of 5-methyl-6-phenylpyridine-2-carbonitrile from example 1.3 in 65 ml of methanol, and the mixture was stirred at 23° C. for 7 hours. 1.5 g of ammonium chloride were then added, and the mixture was stirred at 23° C. for a further 8 hours. After removal of the solvent, MtBE was added and the product was filtered off, which gave 5.4 g of the title compound as a yellowish solid.
$^1$H-NMR (δ, DMSO): 7.5 (m); 7.7 (m); 8.2 (m); 8.3 (m); 9.6 (m).

1.5 2-(5-methyl-6-phenylpyridin-2-yl)-8,7,8,9-tetrahydro-5H-cycloheptapyrimidine 1.3 g of sodium methoxide (30% strength solution in methanol) were added to a solution of 1.5 g (6.1 mmol) of the compound prepared in example 1.4 in 30 ml of methanol. After 30 min, 1.2 g (7.3 mmol) of 2-dimethylamino-methylenecycloheptanone [prepared according to Tetrahedron Letters (1986), 2567] were added, and the mixture was heated at reflux for 2 hours. The reaction solution was then partitioned between water and MtBE. The organic phase was separated off. The solvent was removed under reduced pressure and the residue was chromatographed on silica gel using cyclohexane/MtBE (1:1). This gave 0.72 g of the title compound.
m.p.: 151-154° C.

Example 2

4-[3-methyl-6-(5,6,7,8-tetrahydroquinazolin-2-yl)pyridin-2-yl]benzaldehyde

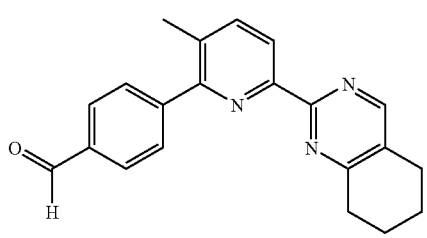

2.1 6-bromo-5-methylpyridine-2-carboxamidine hydrochloride 2.2 g of a 30% strength solution of sodium methoxide in methanol were added to 4.90 g (25 mmol) of 6-bromo-5-methylpyridine-2-carbonitrile [prepared according to US 2003/0087940 A1 or Bioorg. Med. Chem. Lett. (2003), 1571-1574] in 60 ml of methanol, and the mixture was stirred at 23° C. for 7 hours. 1.5 g of ammonium chloride were then added, and the mixture was stirred at 23° C. for a further 8 hours. After removal of the solvent, MtBE was added to the residue and the solid was filtered off. This gave 4.2 g of the title compound as a white solid which was reacted further without purification.

2.2 2-(6-bromo-5-methylpyridin-2-yl)-5,6,7,8-tetrahydroquinazoline 3.6 g of sodium methoxide (30% strength solution in methanol) were added to a solution of 4.2 g (7 mmol) of the compound prepared in example 2.1 in 100 ml of methanol. After 30 min, 3.1 g (20 mmol) of 2-dimethylamino-methylenecyclohexanone [prepared, for example, according to Tetrahedron 50(7) (1994), 2255-64; Synthetic Communications 28(10) (1998), 1743-1753 or Tetrahedron Letters 27(23) (1986), 2567-70] were added, and the mixture was heated at reflux for 2 hours. The reaction solution was then partitioned between water and MtBE. The organic phase was separated off, the solvent was removed under reduced pressure and the residue was chromatographed on silica gel using cyclohexane/MtBE (1:1). This gave 2.2 g of the title compound.

$^1$H-NMR (δ, CDCl$_3$,): 1.8-2.0 (m); 2.5 (s); 2.8 (m); 3.0 (m)

2.3 4-[3-methyl-6-(5,6,7,8-tetrahydroquinazolin-2-yl)pyridin-2-yl]benzaldehyde 0.24 g of 4-formylphenylboronic acid and 0.2 g of sodium carbonate in 3 ml of water were added successively to a solution of 0.2 g of the compound prepared in example 2.2 in 20 ml of ethylene glycol dimethyl ether. After addition of about 50 mg of tetrakis(triphenylphosphine) palladium (0), the mixture was stirred under reflux for 9 hours. A further 0.2 g of 4-formylphenylboronic acid was then added, and the mixture was allowed to react under reflux for a further 10 hours. The reaction solution was then partitioned between water and MtBE. The organic phase was separated off, the solvent was removed under reduced pressure and the residue was chromatographed on silica gel using cyclohexane/MtBE (1:1). This gave 35 mg of the title compound of m.p. 151-154° C.

$^1$H-NMR (δ, CDCl$_3$,): 1.8-2.0 (m, 4H); 2.4 (s, 3H); 2.8 (m, 2H); 3.0 (m, 2H); 7.8 (m, 3H); 8.0 (m, 2H); 8.4 (m, 1H); 8.6 (s, 1H); 10.1 (s, 1H).

Example 3

2-(5-methoxy-6-phenylpyridin-2-yl)-5,6,7,8-tetrahydroquinazoline

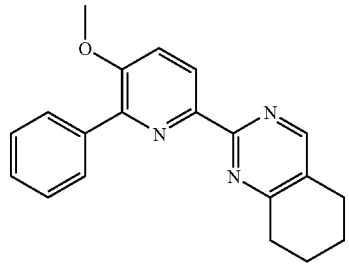

3.1 5-methoxy-6-phenylpyridine-2-carbonitrile 2.1 g of 3-methoxy-2-phenylpyridine [prepared according to Bulletin de la Societe Chimique de France (1974), 1112-16] were initially charged in 60 ml of dichloromethane. At 5° C., 2.4 g of 3-chloroperoxybenzoic acid were added a little at a time, and the mixture was stirred at 5° C. for 2 hours and at 23° C. for 18 hours. The solvent was removed and the residue was then chromatographed on silica gel using methyl tert-butyl ether (MtBE), which gave 1.4 g of 3-methoxy-2-phenylpyridine N-oxide as a crude product in the form of an oil.

The crude product was dissolved in 80 ml of dichloromethane, and 0.9 g of trimethylsilyl cyanide was added dropwise over a period of 5 min and the mixture was stirred at 23° C. for 30 minutes. Over a period of 45 min, a solution of 0.95 g of dimethylcarbamoyl chloride in 10 ml of dichloromethane was then added dropwise, and the mixture was stirred at 23° C. for 18 hours. 40 ml of water and 10 ml of 1 N aqueous sodium hydroxide solution were added carefully to the reaction solution. The pH was then adjusted to 8 using solid sodium carbonate and the organic phase was separated off, washed with water and dried. Removal of the solvent gave, after chromatography on silica gel using cyclohexane/MtBE (3:2), 0.2 g of 5-methoxy-6-phenylpyridine-2-carbonitrile as an oil.

$^1$H-NMR (δ, CDCl$_3$,): 3.9 (s); 7.5 (m); 7.7 (m) and 7.9 (m).

3.2 2-(5-methoxy-6-phenylpyridin-2-yl)-5,6,7,8-tetrahydroquinazoline

The title compound can be prepared analogously to steps 1.4 and 1.5 of example 1 using, instead of 2-dimethylaminomethylenecycloheptanone, the corresponding hexanone.

Example 4

2-(5-chloro-6-phenylpyridin-2-yl)-5,6,7,8-tetrahydroquinazoline

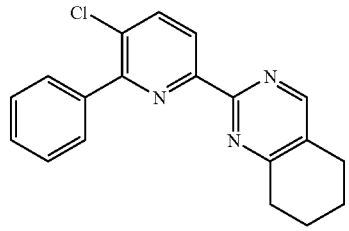

4.1 2-bromo-2-chloropyridine 60 ml of a 33% strength solution of hydrogen bromide in acetic acid were added to 6.3 g of 2,3-dichloropyridine in 50 ml of acetic acid, and the mixture was heated under reflux for 8 hours. A further 42 ml of hydrogen bromide solution were then added. After 6 hours, the reaction had gone to completion. The reaction solution was poured into ice-water and extracted with methylene chloride. The combined organic phases were washed with water and dried, and the solvent was removed under reduced pressure. This gave 8.7 g of product in the form of an oil.

$^1$H-NMR ($\delta$, CDCl$_3$,): 7.2 (m); 7.8 (m) and 8.3 (m).

4.2 3-chloro-2-phenylpyridine 2.35 g of phenylboronic acid and 4.8 g of sodium carbonate in 30 ml of water were added successively to a solution of 2.5 g of 2-bromo-3-methoxypyridine in 80 ml of tetrahydrofuran. After addition of 300 mg of tetrakis(triphenyl-phosphine)palladium(0), the mixture was stirred under reflux for 8 hours. Another 2 g of phenylboronic acid, 2 g of sodium carbonate and 100 mg of tetrakis(triphenylphosphine)palladium(0) were then added, and the mixture was heated under reflux for a further 6 hours. The reaction solution was poured into ice-water and extracted with MtBE. The combined organic phases were dried, the solvent was removed under reduced pressure and the residue was chromatographed on silica gel using cyclohexane/MtBE (9:1). This gave 2.2 g of product in the form of an oil.

$^1$H-NMR ($\delta$, CDCl$_3$,): 7.3 (m); 7.5 (m); 7.8 (m) and 8.6 (m).

4.3 3-chloro-2-phenylpyridine 1-oxide 2.2 g of 3-chloro-2-phenylpyridine were initially charged in 80 ml of dichloromethane. At 5° C., 3.0 g of 3-chloroperoxybenzoic acid were added a little at a time to the mixture, and the mixture was stirred at 5° C. for 2 hours and at 23° C. for 18 hours. The solvent was removed and the residue was then chromatographed on silica gel using MtBE, which gave 1.9 g of product in the form of an oil.

$^1$H-NMR ($\delta$, CDCl$_3$,): 7.2 (m); 7.4-7.6 (m) and 8.3 (m).

4.4 5-chloro-6-phenylpyridine-2-carbonitrile 0.74 g of dimethyl sulfate was added to 1.2 g of 3-chloro-2-phenylpyridine 1-oxide in 5 ml of DMF, and the mixture was allowed to react at 60° C. for 7 hours. After cooling to 23° C., this solution was added dropwise to 0.38 g of potassium cyanide in 10 ml of DMF and stirred at 23° C. for 18 hours. The mixture was subsequently partitioned between MtBE and water, the organic phase was dried, the solvent was removed under reduced pressure and the residue was chromatographed on silica gel using cyclohexane/MtBE (3:2). This gave 0.30 g of product.

$^1$H-NMR ($\delta$, CDCl$_3$,): 7.5 (m); 7.6 (m); 7.7 (m) and 7.9 (m).

4.5 2-(5-chloro-6-phenylpyridin-2-yl)-5,6,7,8-tetrahydroquinazoline

The title compound can be prepared analogously to steps 1.4 and 1.5 of example 1 using, instead of 2-dimethylaminomethylenecycloheptanone, the corresponding hexanone.

Example 5

4-[3-methyl-6-(5,6,7,8-tetrahydroquinazolin-2-yl)pyridin-2-yl]benzonitrile

5.1 6-chloro-5-methylpyridine-2-carbonitrile 2.3 g of 5-methylpyridine-2-carbonitrile were initially charged in 80 ml of dichloromethane. At 5° C., 5.4 g of 3-chloroperoxybenzoic acid were added a little at a time, and the mixture was stirred at 5° C. for 2 hours and at 23° C. for 18 hours. After removal of the solvent, the residue was chromatographed on silica gel using MtBE, which gave 0.8 g of 2-cyano-5-methylpyridine 1-oxide.

0.8 g of 2-cyano-5-methylpyridine 1-oxide was, together with 25 ml of phosphorus oxychloride, heated under reflux for 5 hours. After the reaction had gone to completion, the excess phosphorus oxychloride was removed under reduced pressure. The residue was taken up in methylene chloride, added, with ice-cooling, to water and adjusted to pH 12 using 3 N aqueous sodium hydroxide solution. The organic phase was separated off and dried, and the solvent was removed under reduced pressure. This gave 0.8 g of product.

$^1$H-NMR ($\delta$, CDCl$_3$,): 2.4 (s); 7.6 (m) and 7.7 (m).

5.2 2-(6-chloro-5-methylpyridin-2-yl)-5,6,7,8-tetrahydroquinazoline

Analogously to example 1,4,6-chloro-5-methylpyridine-2-carbonitrile was converted into the 6-bromo-5-methylpyridine-2-carboxamidine hydrochloride. Analogously to example 2.2, this was then used to prepare 2-(6-chloro-5-methylpyridin-2-yl)-5,6,7,8-tetrahydroquinazoline.

$^1$H-NMR ($\delta$, CDCl$_3$,): 8.5 (s); 8.3 (m); 7.7 (m); 3.0 (m); 2.8 (m); 2.4 (s); 1.8-2.0 (m).

5.3 2-(6-bromo-5-methylpyridin-2-yl)-5,6,7,8-tetrahydroquinazoline 8 ml of a 33% strength solution of hydrogen bromide in acetic acid were added to 1 g of 2-(6-chloro-5-methylpyridin-2-yl)-5,6,7,8-tetrahydroquinazoline in 8 ml of acetic acid, and the mixture was heated under reflux for 10 hours. The reaction solution was diluted with water, adjusted to pH 9 using 3 N aqueous sodium hydroxide solution and extracted with MtBE. The combined organic phases were washed with water and dried, and the solvent was removed under reduced pressure. This gave 0.9 g of product.

m.p.: 125-128° C.

5.4 4-[3-methyl-6-(5,6,7,8-tetrahydroquinazolin-2-yl)pyridin-2-yl]benzonitrile The title compound was prepared analogously to example 2.3 by reacting 2-(6-bromo-5-methylpyridin-2-yl)-5,6,7,8-tetrahydroquinazoline with 4-cyanophenyl-boronic acid.

m.p.: 178-182° C.

PREPARATION EXAMPLES FOR STARTING MATERIALS

Preparation Example 1

2-(4-fluorophenyl)-3-methylpyridine 0.70 g of [1,4-bis(diphenylphosphino)butane]palladium (II) chloride was added to a solution of 20.0 g of 2-bromo-3-methylpyridine in 200 ml of tetrahyrdofuran. After 10 min, 128 ml of a 2 molar solution of 4-fluorophenylmagnesium bromide in tetrahydrofuran were added dropwise, and the mixture was heated under reflux for 5 hours. After addition of a further 30 ml of 4-fluorophenylmagnesium bromide solution, the reaction solution was, after 1 hour, added with ice-cooling to aqueous ammonium chloride solution and extracted with ethyl acetate. The combined organic phases were dried, the solvent was removed under reduced pressure and the residue was chromatographed on silica gel using cyclohexane/MtBE (9:1). This gave 17.8 g of 2-(4-fluorophenyl)-3-methylpyridine as an oil.

Preparation Example 2

2-(6-chloro-5-methylpyridin-2-yl)-5,6,7,8-tetrahydroquinazoline a) 5-methylpyridine-2-carboxamidine hydrochloride The compound was prepared from 2-cyano-5-methylpyridine under the conditions given for example 1.4.
$^1$H-NMR (δ, DMSO): 2.4 (m); 7.9 (m); 8.3 (m); 8.6 (m).

b) 2-(5-methylpyridin-2-yl)-5,6,7,8-tetrahydroquinazoline

The compound was prepared from 2-methylpyridine-2-carboxamidine hydrochloride under the conditions given for example 2.2.
$^1$H-NMR (δ, CDCl$_3$,): 1.9 (m); 2.4 (s); 2.7 (m); 3.0 (m); 7.6 (m); 8.4 (m); 8.5 (m); 8.7 (m).

c) 2-(5-methyl-1-oxypyridin-2-yl)-5,6,7,8-tetrahydroquinazoline 1.0 g of 2-(5-methylpyridin-2-yl)-5,6,7,8-tetrahydroquinazoline was initially charged in 10 ml of dichloromethane. At 5° C., 1.4 g of 3-chloroperoxybenzoic acid were added a little at a time, and the mixture was stirred at 5° C. for 2 hours and at 23° C. for 18 hours. After removal of the solvent, the residue was chromatographed on silica gel using MtBE/EtOH (5:2), which gave 0.75 g of product.
$^1$H-NMR (δ, CDCl$_3$,): 8.6 (s); 8.2 (s); 7.5 (m); 7.1 (m); 3.0 (m); 2.8 (m); 2.4 (m); 1.7-1.9 (m).

d) 2-(6-chloro-5-methylpyridin-2-yl)-5,6,7,8-tetrahydroquinazoline 0.75 g of 2-(5-methylpyridin-2-yl)-5,6,7,8-tetrahydroquinazoline were, together with 10 ml of phosphorus oxychloride, heated under reflux for 10 hours. After the reaction had gone to completion, the excess phosphorus oxychloride was removed under reduced pressure. The residue was taken up in methylene chloride and, with ice-cooling, added to water. The organic phase was separated off and dried, and the solvent was removed under reduced pressure. The residue was chromatographed on silica gel using cyclohexane/MtBE (4:1). This gave 80 mg of product.

The compounds of the formula I listed in table B below were prepared by the procedures given above.

TABLE B

| Example | $(R^1)_m$* | $R^2$ | n | $(R^3)_k$* | Phys. Data (m.p. [° C.]; $^1$H-NMR δ [ppm]; MS m/e [M + H$^+$]) |
|---|---|---|---|---|---|
| 1 | H | H | 3 | H | m/e 302 |
| 2 | 4-CHO | methyl | 2 | H | 151-154 |
| 3 | H | OCH$_3$ | 2 | H | 138-141 |
| 4 | H | Cl | 2 | H | 133-136 |
| 5 | 4-CN | methyl | 2 | H | 178-182 |
| 6 | H | methyl | 3 | H | 150-153 |
| 7 | 4-fluoro | H | 3 | H | 90-93 |
| 8 | 4-chloro | methyl | 3 | H | 178-181 |
| 9 | 4-fluoro | methyl | 3 | H | 163-165 |
| 10 | H | methyl | 2 | 7,7-dimethyl | 180-183 |
| 11 | H | H | 4 | H | 81-84 |
| 12 | H | methyl | 4 | H | 152-158 |
| 13 | H | OCH$_3$ | 1 | H | 140-143 |
| 14 | H | OCH$_3$ | 3 | H | 156-159 |
| 15 | H | OCH$_3$ | 4 | H | |
| 16 | 4-F | OCH$_3$ | 1 | H | 148-150 |
| 17 | 4-F | OCH$_3$ | 2 | H | 156-158 |
| 18 | 4-F | OCH$_3$ | 3 | H | 162-164 |
| 19 | 4-Cl | OCH$_3$ | 1 | H | |
| 20 | 4-Cl | OCH$_3$ | 2 | H | |
| 21 | 4-Cl | OCH$_3$ | 3 | H | 136-139 |
| 22 | H | Cl | 1 | H | |
| 23 | H | Cl | 3 | H | 161-164 |
| 24 | H | Cl | 4 | H | |
| 25 | 4-F | Cl | 1 | H | |
| 26 | 4-F | Cl | 2 | H | 142-145 |
| 27 | 4-F | Cl | 3 | H | 143-146 |

TABLE B-continued

| Example | $(R^1)_m$* | $R^2$ | n | $(R^3)_k$* | Phys. Data (m.p. [° C.]; $^1$H-NMR δ [ppm]; MS m/e [M + H$^+$]) |
|---|---|---|---|---|---|
| 28 | 4-F | Cl | 4 | H | |
| 29 | 4-Cl | Cl | 1 | H | |
| 30 | 4-Cl | Cl | 2 | H | |
| 31 | 4-Cl | Cl | 3 | H | |
| 32 | 4-Cl | Cl | 4 | H | |
| 33 | H | F | 1 | H | |
| 34 | H | F | 2 | H | |
| 35 | H | F | 3 | H | |
| 36 | H | F | 4 | H | |
| 37 | 4-F | F | 1 | H | |
| 38 | 4-F | F | 2 | H | |
| 39 | 4-F | F | 3 | H | |
| 40 | 4-F | F | 4 | H | |
| 41 | 4-Cl | F | 1 | H | |
| 42 | 4-Cl | F | 2 | H | |
| 43 | 4-Cl | F | 3 | H | |
| 44 | 4-Cl | F | 4 | H | |
| 45 | H | CF$_3$ | 1 | H | |
| 46 | H | CF$_3$ | 2 | H | |
| 47 | H | CF$_3$ | 3 | H | |
| 48 | H | CF$_3$ | 4 | H | |
| 49 | 4-F | CF$_3$ | 1 | H | |
| 50 | 4-F | CF$_3$ | 2 | H | |
| 51 | 4-F | CF$_3$ | 3 | H | |
| 52 | 4-F | CF$_3$ | 4 | H | |
| 53 | H | OCHF$_2$ | 1 | H | |
| 54 | H | OCHF$_2$ | 2 | H | |
| 55 | H | OCHF$_2$ | 3 | H | |
| 56 | H | OCHF$_2$ | 4 | H | |
| 57 | 4-F | OCHF$_2$ | 1 | H | |
| 58 | 4-F | OCHF$_2$ | 2 | H | |
| 59 | 4-F | OCHF$_2$ | 3 | H | 128-131 |
| 60 | 4-F | OCHF$_2$ | 4 | H | |
| 61 | 4-Cl | CF$_3$ | 1 | H | |
| 62 | 4-Cl | CF$_3$ | 2 | H | |
| 63 | 4-Cl | CF$_3$ | 3 | H | |
| 64 | 4-Cl | CF$_3$ | 4 | H | |
| 65 | 4-Cl | OCHF$_2$ | 1 | H | |
| 66 | 4-Cl | OCHF$_2$ | 2 | H | |
| 67 | 4-Cl | OCHF$_2$ | 3 | H | |
| 68 | 4-Cl | OCHF$_2$ | 4 | H | |
| 69 | 4-CHO | methyl | 3 | H | 151-154 |
| 70 | 4-CN | methyl | 3 | H | 178-181 |
| 71 | 4-CF$_3$ | methyl | 3 | H | 189-192 |
| 72 | 4-F | ethoxy | 2 | H | 135-138 |
| 73 | 4-F | ethoxy | 1 | H | 114-117 |
| 74 | H | ethoxy | 2 | H | 140-143 |
| 75 | H | ethoxy | 3 | H | 102-105 |
| 76 | H | ethoxy | 1 | H | 120-123 |
| 77 | 4-F | ethoxy | 3 | H | 130-133 |
| 78 | 4-F | methyl | 2 | 7,7-dimethyl | 171-173 |
| 79 | 4-F | methyl | 4 | H | 160-162 |
| 80 | 4-Cl | ethoxy | 1 | H | 139-142 |
| 81 | 4-Cl | ethoxy | 3 | H | 139-142 |
| 82 | 4-CH$_3$ | methyl | 3 | H | 56-59 |
| 83 | 4-CHO | methyl | 3 | H | 128-131 |
| 84 | 4-methoxy | methyl | 3 | H | 139-142 |
| 85 | 2,4-difluoro | methyl | 3 | H | 131-134 |
| 86 | 2-Cl | methyl | 3 | H | 120-123 |
| 87 | 2-F | methyl | 3 | H | 123-126 |
| 88 | 4-CH(=NOCH$_3$) | methyl | 3 | H | 143-146 |
| 89 | 4-tert-butyl | methyl | 3 | H | 178-181 |
| 90 | 4-isopropyl | methyl | 3 | H | 135-138 |
| 91 | 2-methyl | methyl | 3 | H | 2.8 (m); 3.1 (m); 7-2-7.3 (m); 7.7 (m) |
| 92 | 4-CN | methyl | 3 | H | 141-144 |
| 93 | 4-C(=NOCH$_3$)(CH$_3$) | methyl | 2 | H | 188-191 |
| 94 | 4-SCH$_3$ | methyl | 2 | H | 160-163 |
| 95 | 3-SCH$_3$ | methyl | 2 | H | 151-154 |
| 96 | 4-Cl | methyl | 2 | 7,7-dimethyl | 181-183 |
| 97 | 4-CF$_3$ | methyl | 2 | 7,7-dimethyl | 189-190 |
| 98 | 4-methyl | methyl | 2 | 7,7-dimethyl | 185-186 |
| 99 | 4-ethyl | methyl | 2 | 7,7-dimethyl | 164-166 |
| 100 | 4-isopropyl | methyl | 2 | 7,7-dimethyl | 181-182 |
| 101 | 4-tert-butyl | methyl | 2 | 7,7-dimethyl | 201 |

TABLE B-continued

| Example | (R¹)$_m$* | R² | n | (R³)$_k$* | Phys. Data (m.p. [° C.]; ¹H-NMR δ [ppm]; MS m/e [M + H⁺]) |
|---|---|---|---|---|---|
| 102 | 4-methoxy | methyl | 2 | 7,7-dimethyl | 199-201 |
| 103 | 4-SCH₃ | methyl | 2 | 7,7-dimethyl | 187-188 |
| 104 | 4-OCF₃ | methyl | 2 | 7,7-dimethyl | 197-198 |
| 105 | 4-ethoxy | methyl | 2 | 7,7-dimethyl | 1.0 (s); 3.0 (m); 4.1 (q); 6.9 (m); 8.2 (m) |
| 106 | 4-propoxy | methyl | 2 | 7,7-dimethyl | 172-174 |
| 107 | 4-isopropoxy | methyl | 2 | 7,7-dimethyl | 183-184 |
| 108 | 4-phenoxy | methyl | 2 | 7,7-dimethyl | 153-155 |
| 109 | 4-nitro | methyl | 2 | 7,7-dimethyl | 1.0 (s); 1.7 (m); 3.0 (m); 8.3 (m); 8.4 (m) |
| 110 | 4-CN | methyl | 2 | 7,7-dimethyl | 212-215 |
| 111 | 4-CHO | methyl | 2 | 7,7-dimethyl | 164-166 |
| 112 | 4-C(H)(=NOCH₃) | methyl | 2 | 7,7-dimethyl | 195-198 |
| 113 | 4-COCH₃ | methyl | 2 | 7,7-dimethyl | 197-199 |
| 114 | 4-C(=NOCH₃)(CH₃) | methyl | 2 | 7,7-dimethyl | 186-187 |
| 115 | 4-C(=NOCH₂H₃)CH₃ | methyl | 2 | 7,7-dimethyl | 174-175 |
| 116 | 4-CO₂CH₃ | methyl | 2 | 7,7-dimethyl | 1.0 (s); 3.95 (s); 3.0 (m); 7.7 (m); 8.35 (m) |
| 117 | 2-F | methyl | 2 | 7,7-dimethyl | 155 |
| 118 | 2-Cl | methyl | 2 | 7,7-dimethyl | 102-106 |
| 119 | 2-methyl | methyl | 2 | 7,7-dimethyl | 126-128 |
| 120 | 2-methoxy | methyl | 2 | 7,7-dimethyl | 128-131 |
| 121 | 2-ethoxy | methyl | 2 | 7,7-dimethyl | 117-120 |
| 122 | 2,3-difluoro | methyl | 2 | 7,7-dimethyl | 140-143 |
| 123 | 2,3-dimethyl | methyl | 2 | 7,7-dimethyl | 153-156 |
| 124 | 2,4-difluoro | methyl | 2 | 7,7-dimethyl | 162-166 |
| 125 | 2-fluoro-4-methyl | methyl | 2 | 7,7-dimethyl | 162-166 |
| 126 | 2-methyl-4-fluoro | methyl | 2 | 7,7-dimethyl | 148-152 |
| 127 | 2,4-dimethoxy | methyl | 2 | 7,7-dimethyl | 134-137 |
| 128 | 2,5-difluoro | methyl | 2 | 7,7-dimethyl | 175-177 |
| 129 | 2,5-dichloro | methyl | 2 | 7,7-dimethyl | 137-140 |
| 130 | 2,5-dimethyl | methyl | 2 | 7,7-dimethyl | 104-110 |
| 131 | 3-fluoro | methyl | 2 | 7,7-dimethyl | 158-160 |
| 132 | 3-chloro | methyl | 2 | 7,7-dimethyl | 174-176 |
| 133 | 3-methyl | methyl | 2 | 7,7-dimethyl | 133-135 |
| 134 | 3-CF₃ | methyl | 2 | 7,7-dimethyl | 127-128 |
| 135 | 3-methoxy | methyl | 2 | 7,7-dimethyl | 143-145 |
| 136 | 3-SCH₃ | methyl | 2 | 7,7-dimethyl | 119-121 |
| 137 | 3-Ethoxy | methyl | 2 | 7,7-dimethyl | 147-151 |
| 138 | 3-isopropoxy | methyl | 2 | 7,7-dimethyl | 127-130 |
| 139 | 3-COCH₃ | methyl | 2 | 7,7-dimethyl | 151-152 |
| 140 | 3-C(=NOCH₃)CH₃ | methyl | 2 | 7,7-dimethyl | 146-148 |
| 141 | 3-C(=NOCH₂CH₃)CH₃ | methyl | 2 | 7,7-dimethyl | 135-140 |
| 142 | 3-CO₂CH₃ | methyl | 2 | 7,7-dimethyl | 132-135 |
| 143 | 3,4-difluoro | methyl | 2 | 7,7-dimethyl | 185-188 |
| 144 | 3,4-dichloro | methyl | 2 | 7,7-dimethyl | 182-186 |
| 145 | 3,4-dimethyl | methyl | 2 | 7,7-dimethyl | 153-156 |
| 146 | 3,4-dimethoxy | methyl | 2 | 7,7-dimethyl | 171-175 |
| 147 | 3-fluoro-4-methyl | methyl | 2 | 7,7-dimethyl | 187-188 |
| 148 | 3-fluoro-4-methoxy | methyl | 2 | 7,7-dimethyl | 200-201 |
| 149 | 3-fluoro-4-ethoxy | methyl | 2 | 7,7-dimethyl | 179-181 |
| 150 | 3-chloro-4-fluoro | methyl | 2 | 7,7-dimethyl | 184 |
| 151 | 3-chloro-4-ethoxy | methyl | 2 | 7,7-dimethyl | 118-120 |
| 152 | 3-chloro-4-isopropoxy | methyl | 2 | 7,7-dimethyl | 133-137 |
| 153 | 3-methyl-4-chloro | methyl | 2 | 7,7-dimethyl | 187 |
| 154 | 3-methyl-4-methoxy | methyl | 2 | 7,7-dimethyl | 177-181 |
| 155 | 3,5-difluoro | methyl | 2 | 7,7-dimethyl | 1.0 (s); 1.7 (m); 2.4 (s); 2.5 (m); 3.0 (m) |
| 156 | 3,5-dichloro | methyl | 2 | 7,7-dimethyl | 118-123 |
| 157 | 3,5-dimethyl | methyl | 2 | 7,7-dimethyl | 115-120 |
| 158 | 3,5-(CF₃)₂ | methyl | 2 | 7,7-dimethyl | 149-151 |
| 159 | 3,4,5-trifluoro | methyl | 2 | 7,7-dimethyl | 194-195 |
| 160 | 4-COCH₃ | methyl | 3 | H | 161-164 |
| 161 | 3,4-dichloro | methyl | 3 | H | 157-160 |
| 162 | 3-Cl | methyl | 3 | H | 123-126 |
| 163 | 3-F | methyl | 3 | H | 121-125 |
| 164 | 3-CH₃ | methyl | 3 | H | 100-103 |
| 165 | 3-OCH₃ | methyl | 3 | H | 115-118 |
| 166 | 3,4-dimethoxy | methyl | 3 | H | 148-151 |
| 167 | 3,5-dichloro | methyl | 3 | H | 2.5 (s); 2.8 (m); 3.1 (m); 8.4 (m); 8.6 (m) |
| 168 | 3-Cl-4-F | methyl | 3 | H | 131-134 |
| 169 | 4-phenoxy | methyl | 3 | H | 161-164 |
| 170 | 3-bromo | methyl | 3 | H | 1.6-1.8 (m); 1.85-2.0 (s); 2.8 (m); 3.1 (m); |

TABLE B-continued

| Example | $(R^1)_m$* | $R^2$ | n | $(R^3)_k$* | Phys. Data (m.p. [° C.]; $^1$H-NMR δ [ppm]; MS m/e [M + H$^+$]) |
|---|---|---|---|---|---|
| 171 | 4-SCH$_3$ | methyl | 3 | H | 147-150 |
| 172 | 3-SCH$_3$ | methyl | 3 | H | 115-118 |
| 173 | 3-CF$_3$ | methyl | 3 | H | 95-98 |
| 174 | 3-chloro-4-isopropoxy | methyl | 3 | H | 99-102 |
| 175 | 3-chloro-4-ethoxy | methyl | 3 | H | 118-121 |
| 176 | 3,5-dimethyl | methyl | 3 | H | 2.8 (m); 3.1 (m); 7.7 (m); 8.3 (m); 8.5 (m) |
| 177 | 3-fluoro-4-methoxy | methyl | 3 | H | 140-143 |
| 178 | 3,4-difluoro | methyl | 3 | H | 155-158 |
| 179 | 2-methoxy | methyl | 3 | H | 173-176 |
| 180 | 4-ethyl | methyl | 3 | H | 151-154 |
| 181 | 3,4-dimethyl | methyl | 3 | H | 2.7 (m); 3.1 (m); 7.1 (m); 7.7 (m); 8.3 (m) |
| 182 | 2,4-dimethoxy | methyl | 3 | H | 2.2 (s); 3.7 (s); 3.8 (s); 6.5 (m); 6.6 (m) |
| 183 | 4-OCF$_3$ | methyl | 3 | H | 156-159 |
| 184 | 2-ethoxy | methyl | 3 | H | 124-127 |
| 185 | 3,5-difluoro | methyl | 3 | H | 170-173 |
| 186 | 3-isopropoxy | methyl | 3 | H | 1.3 (d); 2.4 (s); 4.6 (m); 6.9 (m); 7.1 (m) |
| 187 | 2,3-difluoro | methyl | 3 | H | 132-135 |
| 188 | 2,5-difluoro | methyl | 3 | H | 145-148 |
| 189 | 2,5-dichloro | methyl | 3 | H | 2.2 (s); 2.7 (m); 3.1 (m); 7.7 (m) |
| 190 | 2,3-dimethyl | methyl | 3 | H | 140-143 |
| 191 | 3-methyl-4-fluoro | methyl | 3 | H | 120-123 |
| 192 | 3-CO$_2$CH$_3$ | methyl | 3 | H | 2.2 (s); 2.8 (m); 3.1 (m); 3.9 (s) |
| 193 | 3,4,5-trifluoro | methyl | 3 | H | 155-158 |
| 194 | 2-methyl-4-fluoro | methyl | 3 | H | 2.1 (s); 2.2 (s); 2.7 (m); 3.1 (m); 8.3 (m); 8.5 (m) |
| 195 | 3-methyl-4-methoxy | methyl | 3 | H | 134-137 |
| 196 | 3-methyl-4-chloro | methyl | 3 | H | 134-137 |
| 197 | 3-fluoro-4-methyl | methyl | 3 | H | 157-160 |
| 198 | 4-isopropoxy | methyl | 3 | H | 122-125 |
| 199 | 4-n-butoxy | methyl | 3 | H | 115-118 |
| 200 | 4-n-propoxy | methyl | 3 | H | 1.0 (m); 3.9 (m); 7.0 (m); 7.6 (m); 7.7 (m); 7.95 (m); 8.3 (m); 8.5 (m) |

*Prefixes indicate the respective position of the substituent(s)

Test of the Fungicidal Activity:

For the use examples 1 to 5 the active compounds were prepared separately as a stock solution with 0.25% by weight of active compound in acetone or DMSO. 1% by weight of the emulsifier Wettol® EM 31 (wetting agent having emulsifying and dispersing action based on ethoxylated alkylphenols) was added to this solution, and the solution was diluted with water to the desired concentration.

For use examples 6 to 9, the active compounds were prepared as a stock solution comprising 25 mg of active compound which was made up to 10 ml using a mixture of acetone and/or DMSO and the emulsifier Uniperol® EL (wetting agent having emulsifying and dispersing action based on ethoxylated alkylphenols) in a volume ratio of solvent/emulsifier of 99 to 1. This solution was then made up to 100 ml using water. This stock solution was diluted with the solvent/emulsifier/water mixture described to the active compound concentration given below.

Use Example 1

Activity Against Early Blight Caused by *Alternaria solani*

Leaves of tomato plants of the cultiva "Goldene Prinzessin" were sprayed to runoff point with an aqueous suspension having the concentration of active compounds stated below. The next day, the treated plants were infected with a spore suspension of *Alternaria solani* in a 2% aqueous biomalt solution having a density of 0.17×10$^6$ spores/ml. The test plants were then placed in a water-vapor-saturated chamber at temperatures of from 20 to 22° C. After 5 days, the early blight on the untreated, but infected plants had developed to such an extent that the infection could be determined visually.

In this test, the plants which had been treated with 250 ppm of the active compounds from examples 1, 6, 7, 9 and 11 showed no infection, whereas the untreated plants were 90% infected. The plants which, for comparison, had been treated under the same conditions with 2-(5-methyl-6-(4-fluorophenyl)pyridin-2-yl)-5,6,7,8-tetrahydroquinazoline (compound according to EP-A 259 139) showed an infection of 80%.

Use Example 2

Activity Against Gray Mold on Bell Pepper Leaves Caused by *Botrytis cinerea* with Protective Application Bell pepper leaves of the cultiva "Neusiedler Ideal Elite" were, after 2 to 3 leaves had become well developed, sprayed to runoff point with an aqueous suspension having the concentration of active compounds stated below. The next day, the treated plants were inoculated with an aqueous spore suspension of *Botrytis cinerea* in a 2% aqueous biomalt solution having a density of 1.7×10⁶ spores/ml. The plants were then placed in a climatized chamber at temperatures between 22 and 24° C. and at high atmospheric humidity. After 5 days, the extent of the fungal infection was determined visually by the infected leaf area.

In this test, the plants which had been treated with 250 ppm of the active compounds from examples 6, 7 and 11 showed no infection, whereas the untreated plants were 90% infected.

Use Example 3

Activity Against Mildew of Wheat Caused by *Erysiphe* [Syn. *Blumeria*] *Graminis* Forma Specialis. Tritici Leaves of potted wheat seedlings of the cultiva "Kanzler" were sprayed to runoff point with an aqueous suspension having the concentration of active compounds stated below. 24 h after the spray coating had dried on, the leaves were dusted with the spores of mildew of wheat (*Erysiphe* [syn. Blumeria] graminis form a specialis. tritici). The plants were then placed in a greenhouse at temperatures between 20 and 24° C. and at 60-90% relative atmospheric humidity. After 7 days, the extent of the fungal infection was determined visually by the infected leaf area.

In this test, the plants which had been treated with 250 ppm of the active compound from example 7 were only slightly infected (20%), whereas the untreated plants were 90% infected. The plants which, for the purpose of comparison, had been treated under the same conditions with 2-(5-methyl-6-(4-fluorophenyl)pyridin-2-yl)-5,6,7,8-tetrahydroquinazoline (compound according to EP-A 259 139) showed an infection of 80%.

Use Example 4

Activity Against *Peronospora* of Grapevines Caused by *Plasmopara viticola*

Leaves of potted grapevines were sprayed to runoff point with an aqueous suspension having the concentration of active compounds stated below. The next day, the undersides of the leaves were inoculated with an aqueous sporangia suspension of *Plasmopara viticola*. The plants were then initially placed in a water-vapor-saturated chamber for 48 h and then in a greenhouse at temperatures between 20 and 30° C. After this period of time, the plants were, to promote sporangial eruption, again placed in the water-vapor-saturated chamber for 16 h. The extent of the development of the infection on the undersides of the leaves was then determined.

In this test, the plants which had been treated with 63 ppm of the active compound from example 7 showed no infection, whereas the untreated plants were 90% infected. The plants which, for the purpose of comparison, had been treated under the same conditions with 2-(5-methyl-6-(4-fluorophenyl)pyridin-2-yl)-5,6,7,8-tetrahydro-quinazoline (compound according to EP-A 259 139) showed an infection of 70%.

Use Example 5

Curative Activity Against Brown Rust of Wheat Caused by *Puccinia recondita*

Leaves of potted wheat seedlings of the cultivar "Kanzler" were inoculated with a spore suspension of brown rust (*Puccinia recondita*). The pots were then placed in a chamber at high atmospheric humidity (90 to 95%) and 20 to 22° C. for 24 hours. During this time, the spores germinated and the germ tubes penetrated into the leaf tissue. The next day, the infected plants were sprayed to runoff point with an aqueous suspension having the active compound concentration stated below. The suspension or emulsion had been prepared as described above. After the spray coating had dried, the test plants were cultivated in a greenhouse at temperatures between 20 and 22° C. and at 65 to 70% relative atmospheric humidity for 7 days. The extent of the rust fungus development on the leaves was then determined.

In this test, the plants which had been treated with 250 ppm of the active compound from example 9 showed only minor infection (20% infection), whereas the untreated plants were 90% infected. The plants which, for comparison, had been treated under the same conditions with 2-(5-methyl-6-(4-fluorophenyl)pyridin-2-yl)-5,6,7,8-tetrahydro-quinazoline (compound according to EP-A 259 139) showed an infection of 50%.

Use Example 6

Activity Against Early Blight Caused by *Afternaria solani*

Leaves of potted tomato plants of the cultivar "Goldene Königin" were sprayed to runoff point with an aqueous suspension having the active compound concentration stated below. The next day, the leaves were infected with an aqueous spore suspension of *Alternaria solani* in a 2% strength biomalt solution having a density of 0.17×10⁶ spores/ml. The plants were then placed in a water vapor-saturated chamber at temperatures of 20 to 22° C. After 5 days, the disease on the untreated but infected plants had developed to such an extent that the infection could be determined visually.

In this test, the plants which had been treated with 63 ppm of the active compounds from examples 9, 13, 16, 17, 18, 72, 73, 74, 75, 76, 78, 79, 82, 84, 85, 86, 87, 88, 89, 90, 91, 92, 93 and 95 showed an infection of at most 20%, whereas the untreated plants were 90% infected.

Use Example 7

Activity Against Net Blotch of Barley Caused by *Pyrenophora teres* with 1 Days Protective Application Leaves of potted barley seedlings were sprayed to runoff point with an aqueous suspension having the active compound concentration stated below. 24 hours after the spray coating had dried, the plants were inoculated with an aqueous spore suspension of *Pyrenophora* [syn. *Drechslera*] teres, the net blotch pathogen. The test plants were then placed in the green house at temperatures between 20 and 24° C. and 95 to 100% relative atmospheric humidity. After 6 days, the extent of the development of the disease was determined visually in % by the infected leaf area.

In this test, the plants which had been treated with 63 ppm of the active compounds from examples 4, 9, 13, 16, 17, 18, 21, 23, 26, 27, 72, 73, 74, 75, 76, 77, 78, 79, 80, 81, 82, 83, 84, 85, 86, 87, 88, 89, 90, 91, 92, 93, 94, 95, 96, 98, 102, 105, 119, 120, 121, 122, 124, 126, 127, 128, 136, 137, 138, 139, 143, 146, 151, 157 und 159 showed an infection of at most 20%, whereas the untreated plants were 90% infected.

Use Example 8

Activity Against Grey Mold on Bell Pepper Leaves Caused by *Botrytis cinerea*, Protective Application Bell pepper leaves of the cultivar "Neusiedler Ideal Elite" were, after 2 to 3 leaves were well developed, sprayed to runoff point with an aqueous suspension having the active compound concentration stated below. The next day, the treated plants were inoculated with a spore suspension of *Botrytis cinerea*, comprising $1.7 \times 10^6$ spores/ml in a 20% strength aqueous biomalt solution. The test plants were then placed in a dark climatized chamber at temperatures between 22 and 24° C., and high atmospheric humidity. After 5 days, the extent of the fungal infection was determined visually in % by the infected leaf area.

In this test, the plants which had been treated with 63 ppm of the active compounds from examples 4, 26, 80, 83 and 94 showed an infection of at most 20%, whereas the untreated plants were 90% infected.

Use Example 9

Activity Against Late Blight on Tomatoes Caused by *Phytophthora infestans* with Protection Treatment Leaves of potted tomato plants were sprayed to runoff point with an aqueous suspension having the active compound concentration stated below. The next day, the leaves were infected with an aqueous sporangia suspension of *Phytophthora infestans*. The plants were then placed in a water vapor-saturated chamber at temperatures between 18 and 20° C. After 6 days, the late blight on the untreated but infected control plants had developed to such an extent that the infection could be determined visually in %.

In this test, the plants which had been treated with 63 ppm of the active compounds from examples 98, 117, 118, 119, 120, 122, 124, 125, 126, 127, 128, 129, 130, 133, 134, 135, 136, 138, 139, 141, 142, 143, 144, 145, 146, 147, 150, 151, 152, 156, 157 and 159 showed an infection of at most 20%, whereas the untreated plants were 90% infected.

We claim:
1. A 2-(Pyridin-2-yl)pyrimidine compound of formula I and agriculturally acceptable salts thereof:

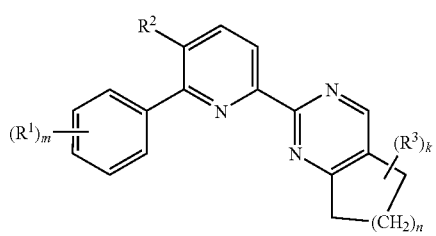

(I)

wherein
k iso, 1, 2 or 3;
m is 0, 1, 2, 3, 4 or 5;
n is 1, 2, 3, 4 or 5;
each $R^1$ independently represents halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_3$-$C_8$-cycloalkyl, $C_1$-$C_4$-alkoxy-$C_1$-$C_4$-alkyl, amino, NHR, $NR_2$, $C(R^a)$=N—$OR^b$, $S(=O)_p A^1$, $C(=O)A^2$ or phenoxy, wherein phenoxy is optionally substituted with halogen or $C_1$-$C_4$-alkyl, and wherein p, R, $R^a$, $R^b$, $A^1$ and $A^2$ have the following meanings:
R is $C_1$-$C_4$-alkyl or $C_1$-$C_4$-alkylcarbonyl,
$R^a$ is hydrogen or $C_1$-$C_4$-alkyl;
$R^b$ is $C_1$-$C_4$-alkyl, $C_3$-$C_4$-alkenyl or $C_3$-$C_4$-alkynyl,
p is 0, 1 or 2,
$A^1$ is $C_1$-$C_4$-alkyl, or if p=2 then $A^1$ is $NH_2$, $C_1$-$C_4$-alkylamino or di-($C_1$-$C_4$-alkyl)amino, and
$A^2$ is hydrogen, hydroxy, $C_1$-$C_4$-alkyl, $C_1$-$C_4$-alkylamino, di-($C_1$-$C_4$-alkyl)amino, $C_2$-$C_4$-alkenyl, $C_1$-$C_4$-alkoxy or $C_1$-$C_4$-haloalkoxy;
or two radicals $R^1$ bound to adjacent carbon atoms are optionally together a group —O-Alk-O—, wherein Alk is linear or branched $C_1$-$C_4$-alkylene, wherein 1, 2, 3 or 4 hydrogen atoms is optionally replaced with halogen;
$R^2$ is $C_1$-$C_4$-haloalkyl, $C_1$-$C_4$-alkoxy, $C_1$-$C_4$-haloalkoxy, hydroxy, halogen, CN or $NO_2$;
wherein $R^2$ is optionally hydrogen or $C_1$-$C_4$-alkyl if at least one of the following conditions is given:
n is 3, 4 or 5,
k is 1, 2 or 3;
and
$R^3$ is $C_1$-$C_4$-alkyl.

2. The compound of formula I according to claim 1, wherein $R^2$ is $C_1$-$C_4$-haloalkyl, $C_1$-$C_4$-alkoxy, $C_1$-$C_4$-haloalkoxy, halogen, CN or $NO_2$.

3. The compound of formula I according to claim 2, wherein $R^2$ is $C_1$-$C_4$-alkoxy, $C_1$-$C_4$-haloalkoxy or halogen.

4. The compound of formula I according to claim 2, wherein n is 1, 2 or 3.

5. The compound of formula I according to claim 1, wherein n is 3, 4 or 5.

6. The compound of formula I according to claim 1, wherein m is 0, 1, 2 or 3.

7. The compound of formula I according to claim 1, wherein $R^1$ is halogen, CN, $C_1$-$C_4$-alkyl, $C_1$-$C_4$-halo alkyl, $C_1$-$C_4$-alkoxy or $C_1$-$C_4$-haloalkoxy.

8. The compound of formula I according to claim 1, wherein one of the radicals $R^1$ is $C(R^a)$=N—$OR^b$ group.

9. The compound of formula I according to claim 1, wherein the group

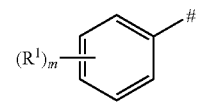

wherein # is the linking position with the pyridine ring, is a radical of formula P

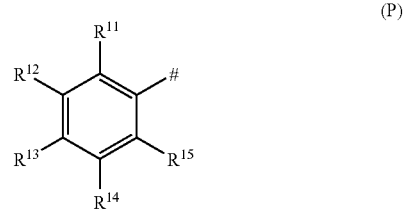

(P)

wherein $R^{11}$ is hydrogen, fluorine, chlorine, $CH_3$, $OCH_3$, $OCHF_2$, $OCF_3$ or $CF_3$;

$R^{12}$, $R^{14}$ are independently a hydrogen, chlorine, fluorine, $CH_3$, $OCH_3$, $OCHF_2$, $OCF_3$ or $CF_3$, wherein one of the radicals $R^{12}$ and $R^{14}$ is optionally $NO_2$, $C(O)CH_3$ or $COOCH_3$;

$R^{13}$ is hydrogen, fluorine, chlorine, cyano, OH, CHO, $NO_2$, $NH_2$, methylamino, dimethylamino, diethylamino, $C_1$-$C_4$-alkyl, $C_3$-$C_8$-cycloalkyl, $C_1$-$C_4$-alkoxy, $C_1$-$C_4$-alkylthio, $C_1$-$C_4$-haloalkyl, $C_1$-$C_4$-haloalkoxy, $CO(A^2)$, wherein $A^2$ is $C_1$-$C_4$-alkyl or $C_1$-$C_4$-alkoxy, or a group $C(R^a)=NOR^b$, wherein $R^a$ is hydrogen or methyl and $R^b$ is $C_1$-$C_4$-alkyl, propargyl or allyl, or $R^{12}$ and $R^{13}$ together form a O—$CH_2$—O group; and $R^{15}$ is hydrogen, fluorine, chlorine or $C_1$-$C_4$-alkyl.

10. The compound of formula I according to claim 9, wherein at least one of the radicals $R^{11}$, $R^{12}$, $R^{13}$, $R^{14}$ or $R^{15}$ is different form hydrogen.

11. A fungicidal composition comprising:
   the compound of formula I according to claim 1 and/or the agriculturally acceptable salts thereof for combating plant pathogenous fungi; and
   a solid or liquid carrier.

12. The fungicidal composition for combating plant pathogenous fungi of claim 11, wherein said composition comprises the agriculturally acceptable salt thereof.

13. A process for combating plant pathogenous fungi, wherein the fungi or the material, crop, soil or seed to be protected from fungal decay is treated with an effective amount of a compound of formula I according to claim 1 and/or an agriculturally acceptable salt thereof.

* * * * *

UNITED STATES PATENT AND TRADEMARK OFFICE
CERTIFICATE OF CORRECTION

PATENT NO. : 7,786,043 B2
APPLICATION NO. : 11/632342
DATED : August 31, 2010
INVENTOR(S) : Wassilios Grammenos et al.

It is certified that error appears in the above-identified patent and that said Letters Patent is hereby corrected as shown below:

Claim 1, column 45, line 62, change "k iso, 1, 2 or 3;" to --k is 0, 1, 2, or 3;--.

Signed and Sealed this
Fourth Day of October, 2011

David J. Kappos
*Director of the United States Patent and Trademark Office*